(12) United States Patent
Koga et al.

(10) Patent No.: US 10,828,194 B2
(45) Date of Patent: Nov. 10, 2020

(54) LACRIMAL DUCT TUBE

(71) Applicant: KANEKA CORPORATION, Osaka (JP)

(72) Inventors: Chihiro Koga, Settsu (JP); Eiji Ogino, Settsu (JP); Fumiyasu Hirai, Settsu (JP); Kohei Fukaya, Osaka (JP); Hidekazu Miyauchi, Osaka (JP); Mariko Matsumoto, Settsu (JP)

(73) Assignee: KANEKA CORPORATION, Osaka (JP)

( * ) Notice: Subject to any disclaimer, the term of this patent is extended or adjusted under 35 U.S.C. 154(b) by 548 days.

(21) Appl. No.: 15/216,443

(22) Filed: Jul. 21, 2016

(65) Prior Publication Data

US 2016/0324690 A1 Nov. 10, 2016

Related U.S. Application Data

(63) Continuation-in-part of application No. PCT/JP2015/051274, filed on Jan. 19, 2015.

(30) Foreign Application Priority Data

Jan. 22, 2014 (JP) ................................. 2014-009688

(51) Int. Cl.
*A61F 9/007* (2006.01)
*A61M 27/00* (2006.01)

(52) U.S. Cl.
CPC ....... *A61F 9/00772* (2013.01); *A61M 27/002* (2013.01); *A61M 2210/0612* (2013.01)

(58) Field of Classification Search
CPC .......................... A61F 9/00772; A61M 27/002
See application file for complete search history.

(56) References Cited

U.S. PATENT DOCUMENTS 5,437,625 A * 8/1995 Kurihashi ........... A61F 9/00772
128/898
6,113,567 A 9/2000 Becker
(Continued)

FOREIGN PATENT DOCUMENTS

CN 102697582 A 10/2012
JP 2539325 B2 10/1996
(Continued)

OTHER PUBLICATIONS

International Search Report (PCT/ISA/210) issued in PCT/JP2015/051274, dated Apr. 21, 2015.
(Continued)

*Primary Examiner* — Leslie R Deak
(74) *Attorney, Agent, or Firm* — Birch, Stewart, Kolasch & Birch, LLP

(57) ABSTRACT

A lacrimal duct tube includes: a pair of tubular members that each have at one end an opening communicating with a lumen; and a connection member that connects the other ends of the tubular members. A base end part including the other end of at least one of the tubular members is tapered down toward the connection member and the base end part has an inlet/outlet port communicating with the lumen of the tubular member. A portion of the base end part constituting peripheral edge of the inlet/outlet port and the connection member are connected together.

26 Claims, 14 Drawing Sheets

(56) References Cited

U.S. PATENT DOCUMENTS

| | | | | |
|---|---|---|---|---|
| 6,117,116 A | * | 9/2000 | Walsh | A61F 9/00772 |
| | | | | 604/264 |
| 2007/0255263 A1 | * | 11/2007 | Sugimoto | A61F 9/00772 |
| | | | | 606/1 |
| 2009/0099626 A1 | * | 4/2009 | de Juan, Jr. | A61L 31/044 |
| | | | | 607/60 |
| 2012/0215153 A1 | | 8/2012 | Fukaya et al. | |
| 2015/0018962 A1 | | 1/2015 | Matsumoto et al. | |
| 2015/0351962 A1 | * | 12/2015 | Fukaya | A61F 9/00772 |
| | | | | 604/8 |
| 2019/0117421 A1 | * | 4/2019 | Kahana | A61M 27/002 |

FOREIGN PATENT DOCUMENTS

| | | | |
|---|---|---|---|
| JP | 2004-202276 A | 7/2004 | |
| JP | 3558924 B2 | 8/2004 | |
| JP | 2005-013698 A | 1/2005 | |
| JP | 2006-181054 A | 7/2006 | |
| JP | 2007-313290 A | 12/2007 | |
| JP | 2010-213957 A | 9/2010 | |
| JP | 2011-200601 A | 10/2011 | |
| WO | WO-0071062 A1 * | 11/2000 | A61F 9/00772 |
| WO | WO 2011/049198 A1 | 4/2011 | |
| WO | WO 2013/111848 A1 | 8/2013 | |

OTHER PUBLICATIONS

Written Opinion (PCT/ISA/237) issued in PCT/JP2015/051274, dated Apr. 21, 2015.

* cited by examiner

Fig. 9(a)
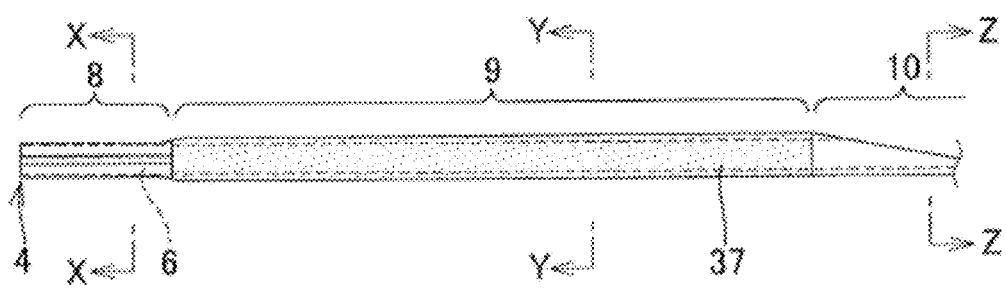
Fig. 9(b)　　　　Fig. 9(c)
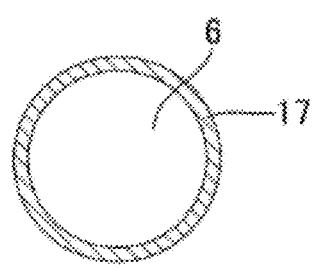 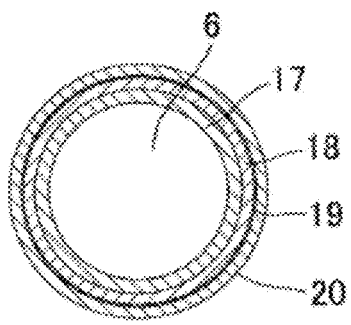
Fig. 9(d)

Fig. 12(a)
Fig. 12(b)
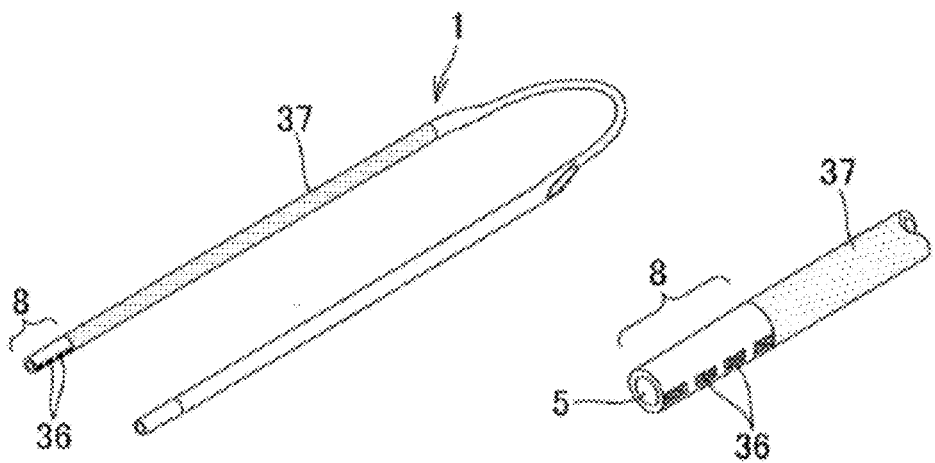
Fig. 13(a)
Fig. 13(b)
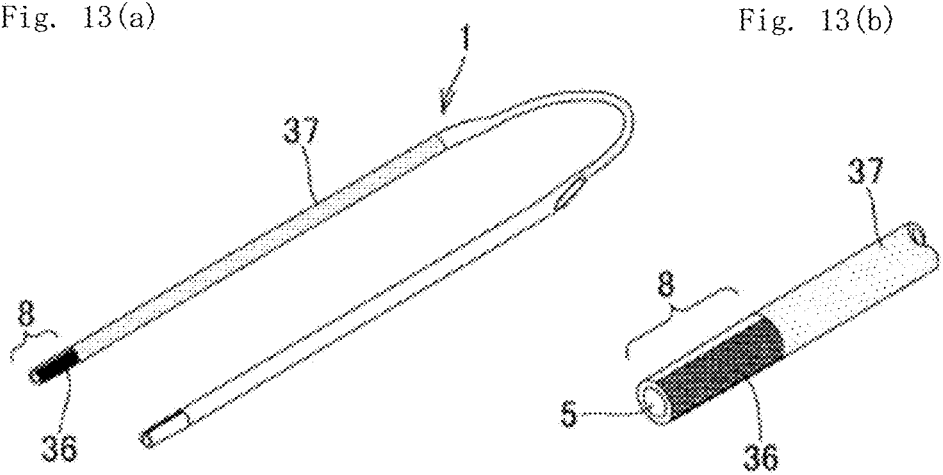

Fig. 14(a)
Fig. 14(b)
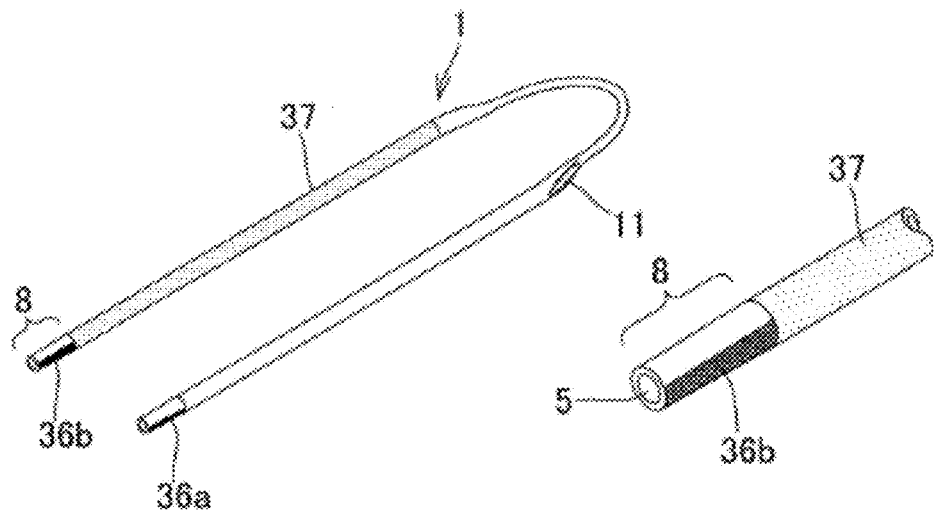
Fig. 15
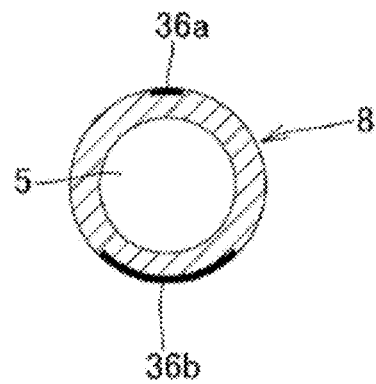

LACRIMAL DUCT TUBE

CROSS REFERENCE TO RELATED APPLICATIONS

This application is a Continuation-in-Part of PCT International Application No. PCT/JP2015/051274, filed on Jan. 19, 2015, which claims priority under 35 U.S.C. 119(a) to Patent Application No. 2014-009688, filed in Japan on Jan. 22, 2014, all of which are hereby expressly incorporated by reference into the present application.

TECHNICAL FIELD

The present invention relates to a lacrimal duct tube for use in treatment of lacrimal duct obstruction.

BACKGROUND ART

Treatment methods for lacrimal duct obstruction resulting in epiphora include: (i) probing by a lacrimal duct bougie, (ii) placement of a lacrimal duct tube; (iii) dacryocystorhinostomy (DCR); (iv) lacrimal canaliculization; (v) nasolacrimal duct plastic surgery; (vi) lacrimal caruncle moving surgery, and the like.

The probing by a lacrimal duct bougie in (i) is intended to insert a narrow tube called bougie into a lacrimal duct to open an obstructed site and reconstruct a flow path for a lacrimal fluid. A lacrimal duct tube (ii) used after that is a lacrimal duct intubation instrument that is placed in the lacrimal duct for maintenance of the flow path and reconstruction of the tissues. These methods are conducted as first treatment in many cases due to its ease of treatment and minimal invasiveness. The treatments (iii) dacryocystorhinostomy (DCR), (iv) lacrimal canaliculization, (v) nasolacrimal duct plastic surgery, and (vi) lacrimal caruncle moving surgery are highly effective but relatively invasive because of the need for creation of incisions in a patient's face or a hole in bones, and thus are conducted as a last resort.

After the probing by the lacrimal duct bougie (i), the lacrimal duct tube for use in the treatment method (ii) is placed in the lacrimal duct for maintaining of the flow path and reconstruction of the tissues. The placement of the lacrimal duct tube (ii) is easy, less invasive as compared to the foregoing treatment methods (iii) to (vi), and highly effective. Among such instruments, there is widely used a lacrimal duct tube in which its central part is formed by a narrow and soft tube or rod and its both sides are formed by hard and thick tubes, as disclosed in Patent Document 1 (for example, refer to Patent Documents 1, 2, and 3).

The lacrimal duct tube includes a tube and a pair of bougies that is inserted into the tube from apertures at both sides of the tube, and the bougies are operated to guide the tube into a lacrimal duct and place the tube there. As shown in FIG. 3, the lacrimal duct includes lacrimal puncta (21 and 22), lacrimal canaliculi (23 and 24), a lacrimal sac (26), a nasolacrimal duct (27), and others. The lacrimal duct tube is inserted into the lacrimal duct.

However, to insert the lacrimal duct tube into the lacrimal duct, the operator needs to grope for intra-lacrimal duct operations with the bougies by feeling of their fingers. If the operator does not have a high level of operating skill, the bougies may break through the tube or make a hole at a site other than in the normal lacrimal duct (creating a false passage), which results in poor therapeutic outcomes.

Accordingly, in the field of treatment of lacrimal duct obstruction of recent years, from the viewpoint of safer and more reliable treatments, a lacrimal duct tube insertion surgery with a combination of sheath-guided endoscopic probing (SEP) and sheath-guided intubation (SGT) has been employed.

According to the SEP technique, a sheath as an outer casing made of Teflon (registered trademark) or polyurethane covering a lacrimal endoscope is preceded the lacrimal endoscope into the lacrimal punctum to rupture into the obstructed site while observing the inside of the lacrimal duct by the lacrimal endoscope. Then, when the tip of the sheath comes out of the opening of the nasolacrimal duct, only the lacrimal endoscope is removed with the sheath left. For example, as shown in FIGS. 1(a) and 1(b), a sheath 30 attached to a lacrimal endoscope 29 is inserted into the lacrimal duct 31 from an upper lacrimal punctum 21 through an upper lacrimal canaliculus 23 to an obstructed site 32 in an inferior nasal meatus 28, and is passed through the obstructed site 32, and then the lacrimal endoscope 29 is removed.

According to the SGI technique, a lacrimal duct tube is connected to the lacrimal punctum-side end of the sheath inserted by SEP, and the tip of the sheath is pulled out of the obstructed site with forceps under observation by the nasal endoscope. Accordingly, the lacrimal duct tube is drawn by the sheath and inserted into the space of the obstructed site opened by SEP. After that, the sheath and the lacrimal duct tube are disconnected to complete the placement of the lacrimal duct tube. For example, a lacrimal duct tube 33 is connected to the sheath 30 as shown in FIG. 2(a), the sheath 30 is pulled from the side opposite to the connection side of the lacrimal duct tube 33 to insert the lacrimal duct tube 33 into the lacrimal duct 31 and let the lacrimal duct tube 33 pass through the obstructed site 32. Next, as shown in FIG. 2(c), the sheath 30 is removed to place the lacrimal duct tube 33 in the lacrimal duct 31.

Next, although not shown, another sheath 30 attached to the lacrimal endoscope 29 is inserted into the obstructed site 32 in the inferior nasal meatus 28 of the lacrimal duct 31 from the lower lacrimal punctum 22 not to be put in the lacrimal duct tube 33 through the lower lacrimal canaliculus 24 and is passed through the obstructed site 32, and then the lacrimal endoscope 29 is removed. Then, an end of the lacrimal duct tube 33 not passing through the obstructed site 32 is connected to the sheath 30, and the sheath 30 is pulled from the side opposite to the connection side of the lacrimal duct tube 33 to let the other end of the lacrimal duct tube 33 pass through the lacrimal duct 31. Lastly, the sheath 30 is removed to place the lacrimal duct tube 33 in the lacrimal duct 31 as shown in FIG. 3.

The foregoing insertion surgery with a combination of SEP and SGI is excellent in safety in that the rupture into the obstructed site can be performed under the lacrimal endoscope, unlike according to the conventional blind technique. In addition, the sheath for use in the SEP technique is made of a high-stiffness material to allow fine operations with direct transfer of force from the hand. The sheath is also advantageous in that there is low risk of breaking the lacrimal endoscope and damaging the fiber in the tip of the sheath during surgery.

According to the SEP technique, however, the lacrimal endoscope is pushed into the sheath and is used to perform complicated procedures such as moving the probe of the lacrimal endoscope covered with the sheath forward and backward like a trombone. Accordingly, it is necessary to form a cutout (generally called "ear") at the end of the sheath such that the sheath can be easily grasped by forceps (for example, refer to Patent Document 4, FIGS. 2, 11). When the sheath is removed from the nose during treatment of the SGI technique, the "ear" gets caught on the wall of the lacrimal duct, and the sheath may damage the wall of the lacrimal duct due to high stiffness of the sheath. In addition, according to the SGI technique, it is very difficult to grasp and pull out the tip of the sheath coming from the obstructed site under observation by the nasal endoscope, which may cause a heavier burden on the patient. Further, the sheath may be embedded in the nose, and in that case, it is necessary to make an aperture in the nose to remove the sheath.

Meanwhile, instead of using the sheath, a lacrimal endoscope may be inserted into the lacrimal duct tube. For example, there is known a lacrimal duct treatment tool including: a lacrimal duct placement main body that has an outer diameter allowing insertion into the lacrimal duct and is formed of a flexible material; and a sheath part that is provided at the lower end of the lacrimal duct placement main body and is composed of a flexible cylindrical body formed of a harder material than that for the lacrimal duct placement main body (refer to Patent Document 5).

However, in the case of using the lacrimal duct treatment tool in the insertion surgery similar to SEP, the lacrimal duct treatment tool is long and is likely to be difficult to operate in general. In addition, it is necessary to separate the main body and the sheath part of the lacrimal duct treatment tool after placement in the lacrimal duct.

As described above, the lacrimal duct tubes for the insertion surgery with a combination of SEP and SGI or the insertion surgery similar to SEP that are currently employed in the treatment of lacrimal duct obstruction cannot be said to be sufficient in safely performing the procedures in a simple and easy manner, and the conventional lacrimal duct tube have room for improvement.

CITATION LIST

Patent Literatures

Patent Document 1: Japanese Patent No. 2539325
Patent Document 2: Japanese Patent No. 3558924
Patent Document 3: JP-A No. 2004-202276
Patent Document 4: JP-A No. 2007-313290
Patent Document 5: JP-A No. 2010-213957

SUMMARY OF INVENTION

Technical Problem

In light of the foregoing circumstances, an object of the present invention is to provide a lacrimal duct tube that can be used favorably for lacrimal duct obstruction treatment equivalent to SEP, specifically, a lacrimal duct tube that can be attached directly to the tip of a lacrimal endoscope, can rupture into the obstructed site of the lacrimal duct more simply and safely without the use of a sheath in the same manner as the SEP technique, and can be placed as it is in the lacrimal duct.

Solution to Problem

The inventors have earnestly conducted studies with the aim of solving the foregoing problems. As a result, the inventors have focused on the base end part at the other end of a tubular member constituting a lacrimal duct tube, and have revealed that, by shaping the tubular member in such a manner that the lacrimal endoscope could be inserted into the tubular member from the base end part, and the base end part could be grasped by forceps and was hard to damage the lacrimal duct even in contact with the lacrimal duct, the lacrimal duct tube became unlikely to get tucked or damaged when operated in the lacrimal duct, and became excellent in procedure in the lacrimal duct and operability of the attached lacrimal endoscope, thereby completing the present invention.

Specifically, the gist of the present invention is as follows:

[1] A lacrimal duct tube comprising: a pair of tubular members that each have at one end an opening communicating with a lumen; and a connection member that connects the other ends of the tubular members, wherein a base end part including the other end of at least one of the tubular members has a taper shape down toward the connection member and the base end part has an inlet/outlet port communicating with the lumen of the tubular member, and a portion of the base end part constituting peripheral edge of the inlet/outlet port and the connection member are connected together.

[2] The lacrimal duct tube according to [1], wherein an area of the inlet/outlet port is larger than an area of an orthogonal cross section of the lumen of the tubular member with respect to a long-axis direction.

[3] The lacrimal duct tube according to [1] or [2], wherein, when a portion of the peripheral edge of the inlet/outlet port closest to the other end side and a portion of the peripheral edge of the inlet/outlet port closest to the one end side are projected onto an orthogonal plane with respect to the long-axis direction of the tubular member, the distance between the portions on the orthogonal plane is larger than the length of inner diameter of the tubular member.

[4] The lacrimal duct tube according to any of [1] to [3], wherein the base end part constituting the peripheral edge of the inlet/outlet port includes a U-shaped portion in the orthogonal plane with respect to the long-axis direction of the tubular member on the other end side of the tubular member.

[5] The lacrimal duct tube according to any of [1] to [4], wherein the peripheral edge of the inlet/outlet port has a step-less surface.

[6] The lacrimal duct tube according to any of [1] to [5], wherein a side surface of the base end part constituting the peripheral edge of the inlet/outlet port and a side surface of the connection member are connected together.

[7] The lacrimal duct tube according to [6], wherein a leading end of the connection member is closer to the one end side than the taper shape formed in the base end part.

[8] The lacrimal duct tube according to any of [1] to [7], wherein, when being projected onto the orthogonal plane with respect to the long-axis direction of the tubular member, the narrowest portion of the taper shape in the base end part is eccentric to a center of an orthogonal cross section of the base end part with respect to the long-axis direction.

[9] The lacrimal duct tube according to any of [1] to [8], wherein the base end part is formed from a single material and is lower in hardness than a remaining part of the tubular member excluding the base end part.

[10] The lacrimal duct tube according to [9], wherein at least a portion of the remaining part of the tubular member excluding the base end part has a multilayered structure.

[11] The lacrimal duct tube according to [10], wherein an outermost layer in the multilayered structure and the base end part are formed from the same material.

[12] The lacrimal duct tube according to [10], wherein the outermost layer in the multilayered structure is formed from a material lower in hardness than the innermost layer.

[13] The lacrimal duct tube according to any of [9] to [12], wherein a circumference of adjacent portions of the base end part and the remaining part of the tubular member excluding the base end part is covered with a reinforcement member across the base end part and the remaining part.

[14] The lacrimal duct tube according to [13], wherein the reinforcement member, the outermost layer in the multilayered structure, and the base end part are formed from the same material.

[15] The lacrimal duct tube according to [14], wherein the connection member, the reinforcement member, the outermost layer in the multilayered structure, and the base end part are formed from the same material.

[16] The lacrimal duct tube according to any of [1] to [15], wherein a terminal end part including the one end of at least one of the tubular members is formed from a colorless material.

[17] The lacrimal duct tube according to [16], wherein a colored portion is formed at a portion of the circumference of the terminal end part formed from the colorless material along a long-axis direction of the tubular member.

[18] The lacrimal duct tube according to [17], wherein the colored portion is formed up to the one end.

[19] The lacrimal duct tube according to [17] or [18], wherein the colored portion is a line or broken line.

[20] The lacrimal duct tube according to any of [17] to [19], wherein the colored portion has a width of 1/50 to 1/3 of an entire circumferential length of the terminal end part.

[21] The lacrimal duct tube according to any of [17] to [20], wherein the colored portion in the tubular member is formed on at least one of the same side as the inlet/outlet port and the opposite side of the inlet/outlet port in a circumferential direction of the tubular member.

[22] The lacrimal duct tube according to [21], wherein the colored portion is formed on the same side as the inlet/outlet port and the opposite side of the inlet/outlet port in the circumferential direction of the tubular member, and a width of one colored portion is different from a width of the other colored portion.

[23] The lacrimal duct tube according to [22], wherein the colored portion with a smaller width is formed on the same side as the inlet/outlet port in the circumferential direction of the tubular member, and the colored portion with a larger width is formed on the opposite side of the inlet/outlet port in the circumferential direction of the tubular member.

[24] The lacrimal duct tube according to any of [17] to [23], wherein a hue of one of the pair of tubular members is a complementary color hue or an adjacent complementary color hue relative to a hue of the colored portion in a hue circle.

[25] The lacrimal duct tube according to [24], wherein a color of a colored tubular member is yellow, and the color of the colored portion is blue.

[26] A lacrimal duct tube including: a pair of tubular members that is each closed at one end and has an opening at the other end; and a connection member connecting the other ends of the tubular members, wherein a base end part including the other end of at least one of the tubular members is tapered down toward the connection member and the base end part has an inlet/outlet port communicating with a lumen of the tubular member, and a portion of the base end part constituting peripheral edge of the inlet/outlet port and the connection member are connected together.

[27] The lacrimal duct tube according to [26], wherein a terminal end part including the one end of at least one of the tubular members is formed from a colorless material.

Advantageous Effects of Invention

According to the lacrimal duct tube of the present invention, the base end part of at least one of the tubular members including the other end is tapered down toward the connection member, and the base end part has the inlet/outlet port communicating with the lumen of the tubular member. Accordingly, the lacrimal endoscope can be inserted into the tubular member from the inlet/outlet port of the base end part to the one end side, and can be used preferably in lacrimal duct obstruction treatment similar to SEP.

In addition, the base end part is tapered down toward the connection member, and a portion of the base end part constituting the peripheral edge of the inlet/outlet port and the connection member are connected together. Accordingly, the base end part is unlikely to hit against the wall of the lacrimal duct. In addition, when the base end part is grasped with forceps during the procedure, the lumen of the tubular member is not crushed. Therefore, it is possible to prevent contact between the lacrimal endoscope inserted into the tubular member and the forceps, and facilitate smooth movement of the lacrimal duct tube which is in a state which the lacrimal endoscope is inserted in forward and backward directions along the lacrimal endoscope. As a result, as compared to the conventional method using a sheath, the rupture into the obstructed site in the lacrimal duct can be performed more simply and safely in a manner similar to SEP, and the lacrimal duct tube can be placed as it is in the lacrimal duct.

According to the lacrimal duct tube of the present invention, the terminal end part including the one end of at least one of the tubular members is formed from a colorless material, thereby making it possible to secure the viewing field of the lacrimal endoscope inserted into the lacrimal duct tube during the procedure.

In addition, the colored portion is formed along the long-axis direction of the tubular member on a portion of the circumference of the terminal end part formed from the colorless material, thereby making it easy to check the position of the terminal end part under observation by the lacrimal endoscope during the procedure.

Further, the hue of the tubular members in the lacrimal duct tube of the present invention is a complementary color hue or an adjacent complementary color hue relative to the hue of the colored portion in the hue circle, thereby making it easy to check the specific position of the tubular member inserted into the lacrimal duct under a dark environment.

BRIEF DESCRIPTION OF DRAWINGS

FIGS. 9(a) to 9(d) are schematic diagram showing an example of the tubular member and cross sections of the leading end side and the base end side of the lacrimal duct tube of the present invention;

FIGS. 12(a) and 12(b) are schematic diagrams showing an example of a colored portion formed at a terminal end part of the lacrimal duct tube of the present invention;

FIGS. 13(a) and 13(b) are schematic diagrams showing an example of a colored portion formed at the terminal end part of the lacrimal duct tube of the present invention;

FIGS. 14(a) and 14(b) are schematic diagrams showing an example of the lacrimal duct tube of the present invention;

FIG. 15 is a schematic diagram showing an example of colored portions formed at the terminal end part of the lacrimal duct tube of the present invention;

DESCRIPTION OF EMBODIMENTS

The present invention will be described later in detail.

Figure 1A:
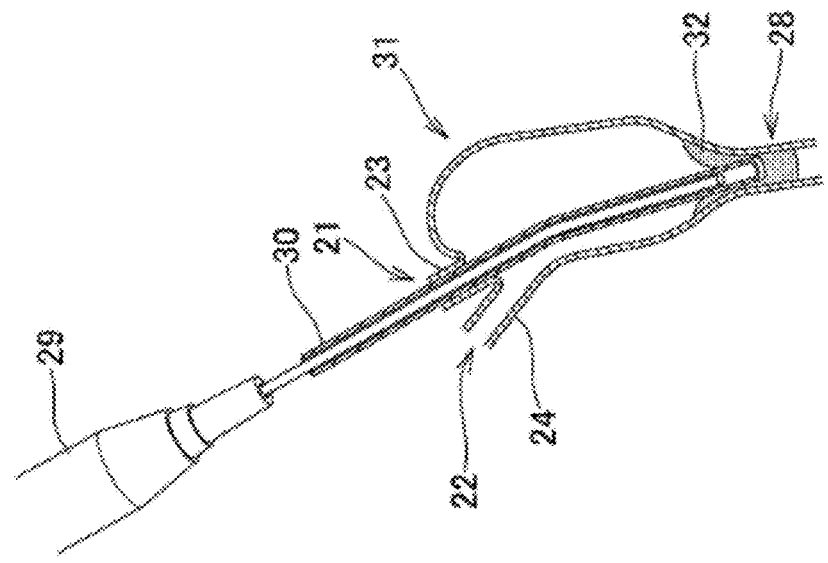
FIGS. 1(a) and 1(b) are schematic illustrative views of an example of a surgical operation on an obstructed site in the lacrimal duct based on SEP.
Figure 1B:
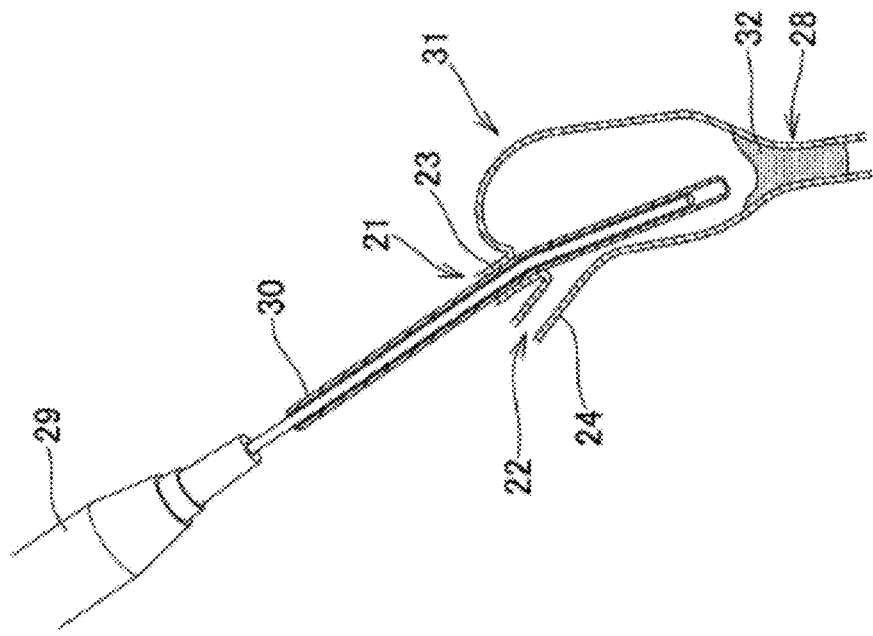
Figure 2C:
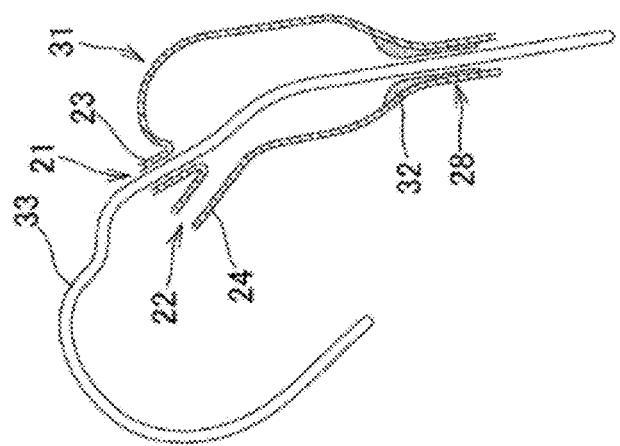
FIGS. 2(a) to 2(c) are schematic illustrative views of an example of a surgical operation on an obstructed site in the lacrimal duct based on SGI.
Figure 2B:
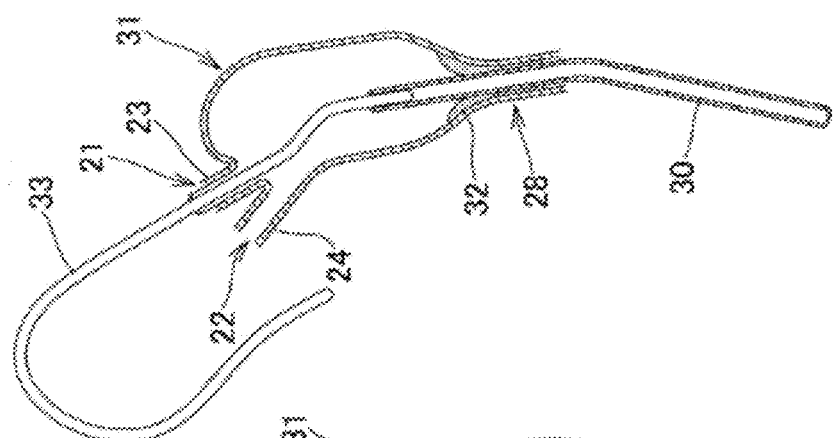
Figure 2A:
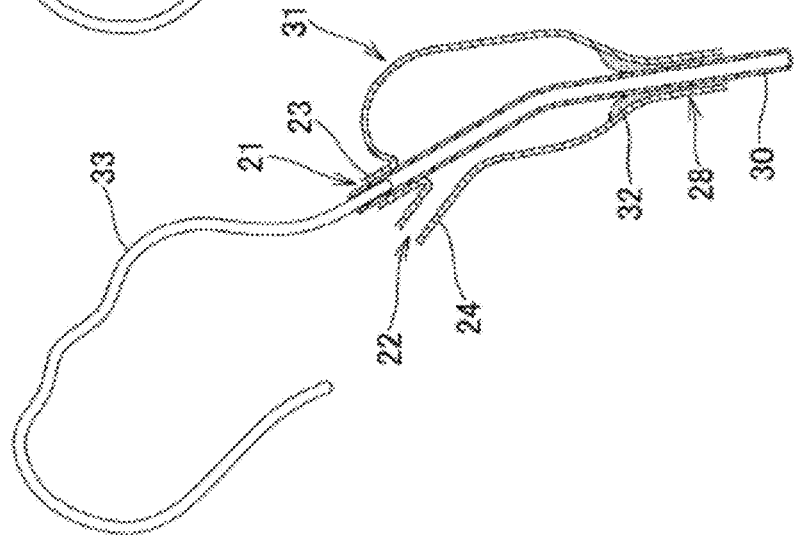
Figure 3:
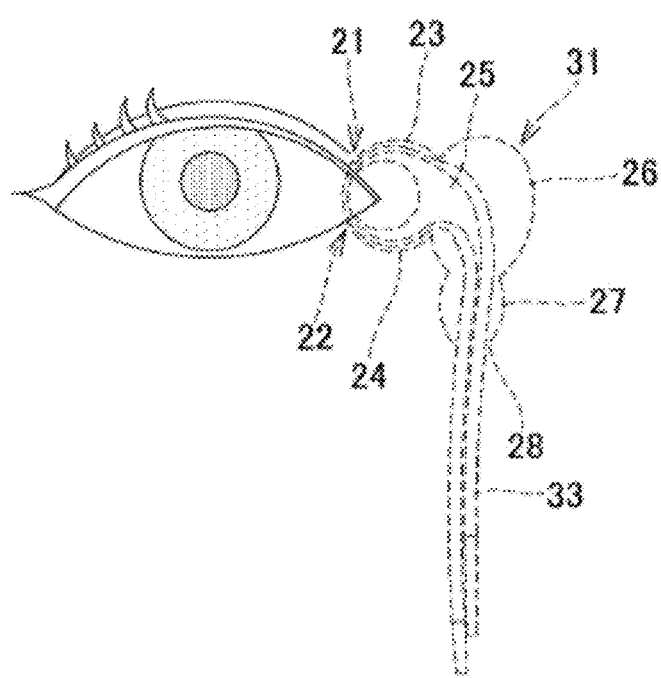
FIG. 3 is an illustrative diagram showing the anatomic structure of the lacrimal duct and the state in which a lacrimal duct obstruction tool is placed in the lacrimal duct.

Lacrimal duct referred to in the present invention is a duct (ocular adnexa) composed of upper/lower lacrimal puncta (21/22), upper/lower lacrimal canaliculi (23/24), a common canaliculus (25), a lacrimal sac (26), a nasolacrimal duct (27), a nasal tract (not shown), and Hasner's valve (not shown), as shown in FIG. 3, which is configured to guide a lacrimal fluid produced by a lacrimal gland (not shown) from an eye surface to an inferior nasal meatus (28). FIG. 3 schematically shows the anatomic structure of the lacrimal duct. In addition, the duct extending from the upper lacrimal punctum (21) through the upper lacrimal canaliculus (23), and the common canaliculus (25) to the inferior nasal meatus (28) is referred to as an upper lacrimal duct, and the duct extending from the lower lacrimal punctum (22) through the lower lacrimal canaliculus (24), and the common canaliculus (25) to the inferior nasal meatus (28) is referred to as a lower lacrimal duct.

The lacrimal duct tube of the present invention is a lacrimal duct tube including: a pair of tubular members that each have at one end an opening communicating with a lumen; and a connection member that connects the other ends of the tubular members, wherein a base end part including the other end of at least one of the tubular members is tapered down toward the connection member and the base end part has an inlet/outlet port communicating with the lumen of the tubular member, and a portion of the base end part constituting peripheral edge of the inlet/outlet port and the connection member are connected together.

The tubular members may be structured as an integrated tube formed from the same resin composition or as a layered-structure tube in which a plurality of layers different in kind of resin is stacked in a thickness direction.

There is no particular limitation on the resin constituting the tubular members. The resin may be any of resin compositions such as, but not limited to, polyethylene, silicone, polyamide elastomer, polyurethane, isobutylene copolymer, and polymer alloy thereof, for example.

In the present invention, there is no particular limitation on the alloy. For example, in the case of using an alloy of polyurethane and isobutylene copolymer, the hardness of the tube can be adjusted by regulating the ratio between the isobutylene block copolymer (A) and the thermoplastic polyurethane resin (B). As the ratio of the thermoplastic polyurethane resin (B) to the isobutylene block copolymer (A) becomes higher, the hardness of the tube increases. From the viewpoints of antithrombogenicity, surface smoothness, and flexibility, it is preferred that 1 weight % or more of the isobutylene block copolymer (A) is included (that is, the ratio of the isobutylene block copolymer (A) to the thermoplastic polyurethane resin (B) is (A)/(B)=1/99 to 99/1 by weight). Above all, from the viewpoint of abrasion resistance, the ratio of the isobutylene block copolymer (A) to the thermoplastic polyurethane resin (B) is preferably (A)/(B)=1/99 to 70/30 by weight. In particular, from the viewpoint of compression stress, the ratio of the isobutylene block copolymer (A) to the thermoplastic polyurethane resin (B) is preferably (A)/(B)=1/99 to 50/50 by weight. The resin composition for the integral tubes for use in the present invention may be composed only of the isobutylene block copolymer (A) and the thermoplastic polyurethane resin (B) or may be mixed with other components.

The isobutylene block copolymer (A) is preferably "SIBSTAR102T" produced by Kaneka Corporation, which is a styrene-isobutylene-styrene block copolymer (hereinafter, also called SIBS). The thermoplastic polyurethane resin (B) (hereinafter, also called TPU) is preferably "Miractran E385PNAT" produced by Nippon Miractran Co., Ltd. or "Tekotan TT1074A" produced by Lubrizol Corporation, which are ether aromatic cyclic polyurethanes, "Tecoflex EG100A" or "Tecoflex EG85A" produced by Lubrizol Corporation, which are ether cycloaliphatic polyurethanes, or "Karubotan PC3575A" produced by Lubrizol Corporation, which is a polycarbonate polyurethane.

When the tubular members are tubes with a layered structure in the thickness direction, the resin used for the layers may be different. For example, polyethylene is preferably used as a high-stiffness resin for the inner layers to improve the pushability of the lacrimal duct tube at the time of treatment of an insertion surgery. In addition, polyurethane is preferably used as a softer resin for the outer layers at portions to be in contact with the lacrimal duct.

In the layered structure having three layers, polyurethane is used for the outermost layer, adhesive polyethylene is used for the intermediate layer, and high-stiffness polyethylene is used for the innermost layer. This advantageously provides the pushability for the rupture into the obstructed site and the safety of the operation in the lacrimal duct.

In the case of a layered structure with four or more layers, it is also preferable to use polyurethane for the outermost layer and high-stiffness polyethylene for the innermost layer.

The layers are welded over the entire long-axis direction of the tubular member. This maintains the continuity of stiffness, makes kinks less likely to occur, easily transfers force from the other end side to the one end side at the time of insertion of the lacrimal duct tube, and provides excellent operability.

The lumen of the tubular member constitutes a space for accommodating a lacrimal duct endoscope inserted through the inlet/outlet port formed at the base end part of the tubular member when the lacrimal duct tube is inserted into the lacrimal duct. In addition, the lumen of the tubular member constitutes a flow path for body fluids such as tears through the inlet/outlet port formed at the base end part of the tubular member when the lacrimal duct tube is placed in the lacrimal duct.

The opening at the one end of the tubular member constitutes part of the flow path for body fluids such as tears when the lacrimal duct tube is placed in the lacrimal duct, and ensures the viewing field of the lacrimal endoscope through the opening when the leading end of the lacrimal endoscope inserted through the inlet/outlet port at the base end part up to the vicinity of the opening. This prevents the problem that the tube generates a false passage to injure mucous membranes and the like and cause bleeding.

The outer diameter of the tubular member merely needs to fall within the range in which it can be inserted into the lacrimal duct. For example, the tubular member with a maximum outer diameter of 0.8 to 1.7 mm is suitable for a wide range of patients' lacrimal ducts regardless of their nationalities and genders.

There is no particular limitation on the length of the tubular members as far as the length is almost the same as those of commercially available lacrimal duct tubes.

The base end part including the other end of the tubular member is provided on the other end side of the tubular member. In the lacrimal duct tube, the base end part of at least one of the tubular members is tapered down toward the connection member and has the inlet/outlet port communicating with the lumen of the tubular member.

The base end part of the tubular member may be formed from a material different from the part other than the base end part (the remaining part) or may be formed from the same material. The remaining part of the tubular member is composed of the terminal end part including the one end of the tubular member and a main body as a primary part of the tubular member.

The base end part may be formed by butting the end portion of another tube against the other end of the tube constituting the terminal end part and the main body of the tubular member and thermally welding the two tubes, or may be formed by fitting the other end of the tube constituting the terminal end part and the main body of the tubular member into the lumen of the tube for the base end part and thermally welding the two tubes.

The base end part as a part of the tubular member is tapered down toward the connection member to be connected to the base end part. The taper shape may be formed by cutting the tube obliquely, or cutting the surface of the tube stepwise, or the like, although there is no limitation on the taper shape (the oblique shape or the taper shape can be formed by any method other than cutting, for example).

The base end part can include a U-shaped portion in a orthogonal plane relative to the long-axis direction of the tubular member at the other end side of the tubular member, thereby to increase the area of the inlet/outlet port and facilitate insertion and removal of the lacrimal endoscope as compared to the case of cutting the base end part in another shape.

Although there is no particular limitation on the angle of the cutting, the surface formed by the cutting is preferably a step-less surface to significantly reduce situations in which the base end part gets caught on the lacrimal duct wall.

In addition, by adjusting the position of the narrowest portion of the taper shape in the base end part projected onto the orthogonal plane relative to the long-axis direction of the tubular member in such a manner as to be eccentric to the center of the orthogonal cross section relative to the long-axis direction of the base end part, it is possible to further increase the area of the inlet/outlet port and facilitate insertion and removal of the lacrimal endoscope.

The inlet/outlet port is formed with the peripheral edge formed by cutting the base end part as described above. The inlet/outlet port is used to insert the lacrimal endoscope into the lumen of the lacrimal duct tube and constitutes a portion of a flow path for a body fluid such as tear when being placed in the lacrimal duct.

The area of the inlet/outlet port is preferably larger than the area of the orthogonal cross section relative to the long-axis direction of the lumen of the tubular member because the lacrimal endoscope becomes easy to insert into the inlet/outlet port, and when the lacrimal duct tube is placed in the lacrimal duct, a flow of a body fluid such as tears can be properly maintained.

The area of the inlet/outlet port may be calculated from the video obtained by shooting the inlet/outlet port and its surroundings with the use of a commercially available microscope at a plurality of angles or may be calculated using dedicated calculation software supporting three-dimensional shapes. The area of the cutting surface of the tubular member may be calculated as the area of the orthogonal cross section relative to the long-axis direction of the lumen section in the same manner as described above.

When a portion of the peripheral edge of the inlet/outlet port closest to the other end side and a portion of the peripheral edge of the inlet/outlet port closest to the one end side are projected onto the orthogonal plane relative to the long-axis direction of the tubular member, the distance between the portions on the orthogonal plane is preferably larger than the length of the inner diameter of the tubular member (the diameter of the lumen) because the trajectory of the lacrimal endoscope is easier to be secured as compared to the case where the inlet/outlet port is formed on the side wall of the tubular member.

When the inlet/outlet port is formed on the side wall of the tubular member, the distance between the portions is about 0.

The length of the base end part may be about 2 to 10 mm although there is no particular limitation.

There is no particular limitation on the resin for forming the base end part. The resin may be any of resin compositions such as, but not limited to, silicone, polyamide elastomer, polyurethane, isobutylene copolymer, and polymer alloy thereof, for example.

In the present invention, there is no particular limitation on the alloy. For example, in the case of using an alloy of polyurethane and isobutylene copolymer, the hardness of the tube can be adjusted by regulating the ratio between the isobutylene block copolymer (A) and the thermoplastic polyurethane resin (B). As the ratio of the thermoplastic polyurethane resin (B) to the isobutylene block copolymer (A) becomes higher, the hardness of the tube increases. From the viewpoints of antithrombogenicity, surface smoothness, and flexibility, it is preferred that 1 weight % or more of the isobutylene block copolymer (A) is included (that is, the ratio of the isobutylene block copolymer (A) to the thermoplastic polyurethane resin (B) is (A)/(B)=1/99 to 99/1 by weight). Above all, from the viewpoint of abrasion resistance, the ratio of the isobutylene block copolymer (A) to the thermoplastic polyurethane resin (B) is preferably (A)/(B)=1/99 to 70/30 by weight. In particular, from the viewpoint of compression stress, the ratio of the isobutylene block copolymer (A) to the thermoplastic polyurethane resin (B) is preferably (A)/(B)=1/99 to 50/50 by weight. The resin composition may be composed only of the isobutylene block copolymer (A) and the thermoplastic polyurethane resin (B) or may be mixed with other components.

The isobutylene block copolymer (A) is preferably "SIBSTAR102T" produced by Kaneka Corporation, which is a styrene-isobutylene-styrene block copolymer (hereinafter, also called SIBS). The thermoplastic polyurethane resin (B) (hereinafter, also called TPU) is preferably "Miractran E385PNAT" produced by Nippon Miractran Co., Ltd. or "Tekotan TT1074A" produced by Lubrizol Corporation, which are ether aromatic cyclic polyurethanes, "Tecoflex EG100A" or "Tecoflex EG85A" produced by Lubrizol Corporation, which are ether cycloaliphatic polyurethanes, or "Karubotan PC3575A" produced by Lubrizol Corporation, which is a polycarbonate polyurethane.

In the tubular members of the lacrimal duct tube of the present invention, properly selecting the resins for the base end part and the other part (the remaining part) produces advantageous effects.

For example, when the base end part is formed from a single material and is lower in hardness than the remaining part excluding the base end part, it is easy to grasp the base end part with forceps while making the base end part hard to break.

By forming at least a portion of the remaining part excluding the base end part in a multilayered structure, it is possible to expand the range of resin choice. For example, by using a low-hardness resin for the outer layers, it is possible to significantly reduce the possibility of causing damage to the lacrimal duct in contact with the lacrimal duct, and by using a high-hardness resin for the inner layers, it is possible to allow the lacrimal duct tube to easily rupture into the obstructed site in the lacrimal duct.

In addition, by forming the outermost layer in the multilayered structure and the base end part from the same material, the tubes consisting the remaining part and the base end part of the tubular member are welded and integrated to provide high adhesion property and further reduce the possibility of breaking the adhesion of the connection portion between the remaining part and the base end part during the procedure.

Further, the outermost layer in the multilayered structure is formed from a material lower in hardness than that for the innermost layer, thereby significantly reducing the possibility of damaging the lacrimal duct during the procedure.

In the lacrimal duct tube of the present invention, a portion of the base end part constituting the peripheral edge of the inlet/outlet port and the connection member are connected together.

The connection member is intended to connect the other ends of the two tubular members. There is no particular limitation on the diameter of the connection member as far as it is smaller than the diameter of the tubular member.

The connection member needs to be composed of a flexible resin, and the resin may be any one of resin compositions such as, but not limited to, silicone, polyamide elastomer, polyurethane, isobutylene copolymer, and alloys thereof, for example.

There is no particular limitation on the length of the connection member as far as the length is almost the same as those of commercially available lacrimal duct tubes.

To connect the tubular member and the connection member, the end portion of the base end part as a portion of the tubular member and the end portion of the connection member may be brought into abutment with each other. However, from the viewpoint of making the connection surfaces larger and enhance the strength of the connected spots, a side surface of the base end part constituting the peripheral edge of the inlet/outlet port (for example, a side surface opposite to the inlet/outlet port in the circumferential direction of the tubular member) and a side surface of the connection member are preferably connected together.

In addition, when the base end part and the connection member are connected by the side surfaces, the position of the leading end of the connection member is preferably adjusted to be closer to the one end side than the taper shape formed at the base end part, thereby to increase the strength of the base end part with the taper shape by the connection member. Further, the position of the leading end of the connection member is preferably adjusted to be further closer to the one end side than the connection portion of the base end part and the remaining part of the tubular member, thereby to increase the strength of the connection portion of the base end part and the remaining part as well by the connection member.

The circumference of the adjacent portions of the base end part and the remaining part of the tubular member excluding the base end part may be covered with a reinforcement member across the base end part and the remaining part.

The reinforcement member may be a tube formed from the same material as the resin material for the base end part and the remaining part or an easy-to-weld material, from the viewpoint of ease of integration with the base end part and the remaining part.

In particular, when the remaining part of the tubular member excluding the base end part has a multilayered structure, the outermost layer in the multilayered structure, the base end part, and the reinforcement member can be formed from the same material to further enhance the strength of connection between the base end part and the remaining part and increase the rupturing force of the lacrimal duct tube. In addition, the outermost layer and the base end part of the tubular member having a multilayered structure, the reinforcement member, and the connection member may be formed from the same material to further increase the strength of the entire lacrimal duct tube and reduce the possibility of breaking the parts during the procedure.

The lumen of the tubular member near the opening may be narrowed (decreased in diameter) and engaged with the leading end of the lacrimal endoscope inserted from the inlet/outlet port. With this structure, the operator can feel resistance resulting from the engagement of the lacrimal endoscope and the lumen near the opening and recognize the position of the terminal end part by the feel.

In the lacrimal duct tube of the present invention, the terminal end part including the one end of at least one of the tubular members is formed from a colorless material. Accordingly, it is possible to observe the state of the outside of the tube by the lacrimal endoscope not only through the opening of the tubular member but also through the wall surface of the tubular member while the lacrimal endoscope is inserted into the lacrimal duct tube.

The colorless material for the terminal end part may be a completely colorless, transparent material or a material that has some color derived from the constituent resin but can be seen through to an extent that the state of the outside of the tube can be observed through the wall portion from the lacrimal endoscope in the lumen (for example, a translucent blue material).

There is no particular limitation on the range of the entire length of the terminal end part. The range may be 2 to 10 mm from the one end.

In at least one of the tubular members, one or more colored portions are formed along the long-axis direction of the tubular member at a portion of the circumference of the terminal end part formed from the colorless material. Accordingly, it is possible to observe the state of the outside of the tube by the lacrimal endoscope not only through the opening of the tubular member but also through the wall surface of the tubular member, and check the position of the terminal end part during the procedure.

Further, when the colored portion is formed up to the one end of the tubular member, it is also possible to check the position of the one end of the tubular member in the lacrimal duct during the procedure.

Although there is no particular limitation, the shape of the colored portion may be a line or broken line. This makes it easy to observe and recognize the position and state of the terminal end part of the tubular member by the lacrimal endoscope in the lumen of the tubular member, thereby providing the advantage of enabling accurate insertion of the lacrimal duct tube.

By setting the width of the colored portion from $1/50$ to $1/3$ of the entire circumferential length of the terminal end part, it is easier to observe and recognize the position and state of the terminal end part of the tubular member inserted into the lacrimal duct by the lacrimal endoscope in the lumen of the tubular member during the procedure. The width of the colored portion is more preferably from $1/20$ to $1/5$.

When the colored portion in the tubular member is formed on at least one of the same side as the inlet/outlet port and the opposite side of the inlet/outlet port in the circumferential direction of the tubular member, it is also possible to check the orientation of the terminal end part from the position of the colored portion observable from the lacrimal endoscope and the position of the inlet/outlet port of the base end part.

In particular, in the case where the colored portion is formed on the same side as the inlet/outlet port and the opposite side of the inlet/outlet port in the circumferential direction of the tubular member, even when the terminal end part is deformed at the time of rupture into the obstructed site in the lacrimal duct, it is possible to accurately recognize the deformed state of the terminal end part and the positional relationship between the opening and the lacrimal endoscope.

Further, by changing the width of the plurality of colored portions, for example, such that the colored portion with a small width (narrow colored portion) is formed on the same side as the inlet/outlet port in the circumferential direction of the tubular member and the colored portion with a large width (wide colored portion) is formed on the opposite side of the inlet/outlet port in the circumferential direction of the tubular member, it becomes easier to check the orientation of the lacrimal duct tube and reliably insert the lacrimal duct tube into the desired place without going in the wrong direction. As a matter of course, the same effect can be produced even when the wide colored portion is formed on the same side as the inlet/outlet port and the narrow colored portion is formed on the opposite side of the inlet/outlet port in the circumferential direction of the tubular member. However, forming the wide colored portion on the opposite side of the inlet/outlet port in the circumferential direction of the tubular member would make it possible to recognize the orientation of the inlet/outlet port, thus the orientation of the lacrimal duct tube in a relatively easy manner, and facilitate the accurate insertion surgery.

Although there is no particular limitation on the color of the colored portions, the nasal cavity is generally in red and therefore the color of the colored portions is adjusted to a complementary color hue or an adjacent complementary color hue relative to red in the hue circle, such as blue, cyan, or the like, for example, such that the colored portions are easy to visually check.

The colored portion may be provided on the terminal end part of at least one of the tubular members or on the terminal end parts of the two tubular members. When the colored portions are provided on the two tubular members, the colors of the colored portions are identical or different. When the colored portions are provided as a plurality of lines or broken lines, the colors of the lines may be identical or different.

In the tubular member having the colored portion, not only the terminal end part but also the entire circumference of the tubular member ranging from the colored portion to the other end side may be colored.

According to the conventional procedure using a sheath, it is difficult to insert the sheath in the dark, obstructed lacrimal duct of a complicated shape, even with the use of the lacrimal endoscope. In this case, the sheath or the like may stick to the mucous membrane to form a false passage or the sheath may be inserted wrongly into the existing false passage.

However, when the entire circumference of the tubular member ranging from the colored portion to the other end side is colored as described above, it is possible to check the position of the tubular member first inserted in the lacrimal duct by the lacrimal endoscope in the tubular member inserted later, and perform the accurate insertion surgery with the checked position as a guide. This prevents the formation of a false passage and the like.

When the entire circumference of the tubular member ranging from the colored portion to the other end side is colored, the color of the colored portion on the other end side may be adjusted to a complementary color hue or an adjacent complementary color hue relative to the hue of the colored portion in the hue circle, such as yellow, yellow green, green, or the like, for example.

In particular, it is preferable that the color of the colored portion is blue and the color of the tubular member on the colored other end side is yellow, from the viewpoint of ease of checking by the lacrimal endoscope.

The colored portion may be fabricated by extrusion molding of a line-included tube with a molding die, a method by which a colored solid tube is thermally welded at the desired position of the tubular member, or the like, although there is no particular limitation on the fabrication method.

The coloring of the colored portion to the other end side of the tubular members may be given in at least one of the tubular members or both of the two tubular members. When the coloring is given to the two tubular members, the colors may be identical or different.

In the case where the coloring is given to the two tubular members, when the position of the tubular member first inserted into the lacrimal duct is checked through the lacrimal endoscope in the tubular member inserted later, the color of the tubular member first placed stands out in the inner surface of the nasal cavity. Accordingly, the tubular member can be checked more clearly in the dark lacrimal duct to enhance the position accuracy of the tubular member to be placed later. In addition, depending on the colors applied to the two tubular members, the tubular members can be used without the colored portions at the terminal end parts. The colors may be yellow, lime green, green, and the like.

The lacrimal duct tube of the present invention may have a hydrophilic coating on the surfaces of the tubular members and the connection member from the viewpoint of excellent insertability into the lacrimal duct and operability in the lacrimal duct.

The hydrophilic coating for use in the hydrophilic-coated portion is intended to provide lubricity in contact with blood or tear fluid, reduce resistance at the time of insertion into the lacrimal duct, and realize favorable operability in the lacrimal duct. There is no particular limitation on the kind of the hydrophilic coating. Preferably, hydrophilic polymers such as poly(2-hydroxyethyl methacrylate), polyacrylamide, polyvinyl pyrrolidone, polyalkylene glycol, monomethoxy polyalkylene glycol, or blends thereof can be used.

There is no particular limitation on the lacrimal endoscope for use in the present invention as far as it is usable for lacrimal duct obstruction treatments.

In addition, a lacrimal duct tube operation tool other than the lacrimal endoscope may be used at the time of insertion of the lacrimal duct tube of the present invention into the lacrimal duct. Such a lacrimal duct tube operation tool may be an operative bar such as a bougie, for example.

A plurality of embodiments of lacrimal duct tube according to the present invention will be described below with reference to the drawings. However, the present invention is not limited to these embodiments.

Figure 4A:
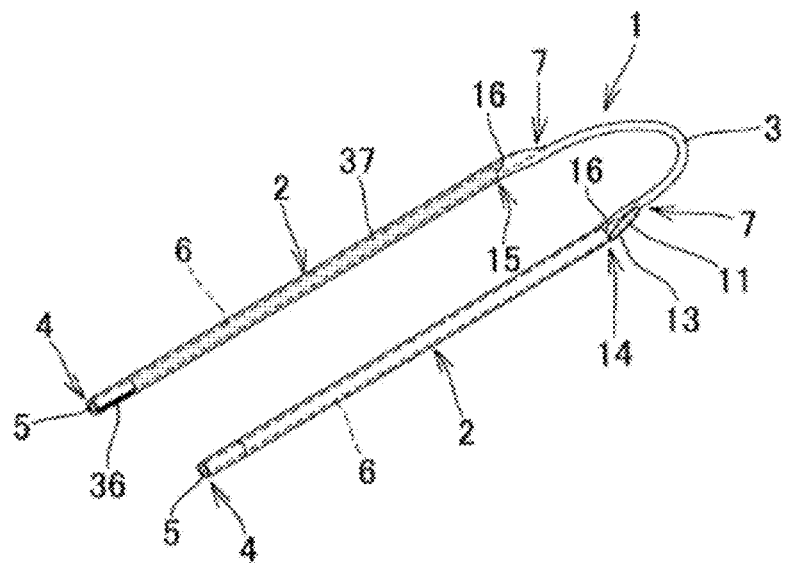
FIGS. 4(a) to 4(c) are schematic views of an example of a lacrimal duct tube of the present invention.
Figure 4B:
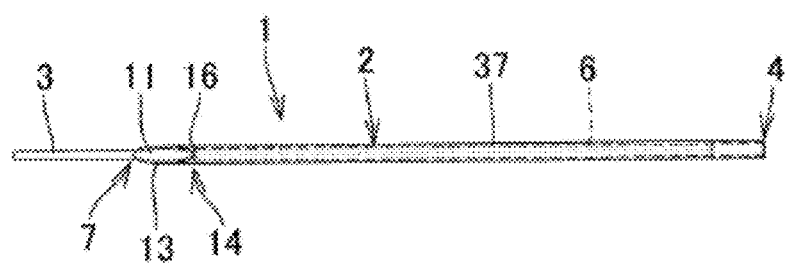
Figure 4C:
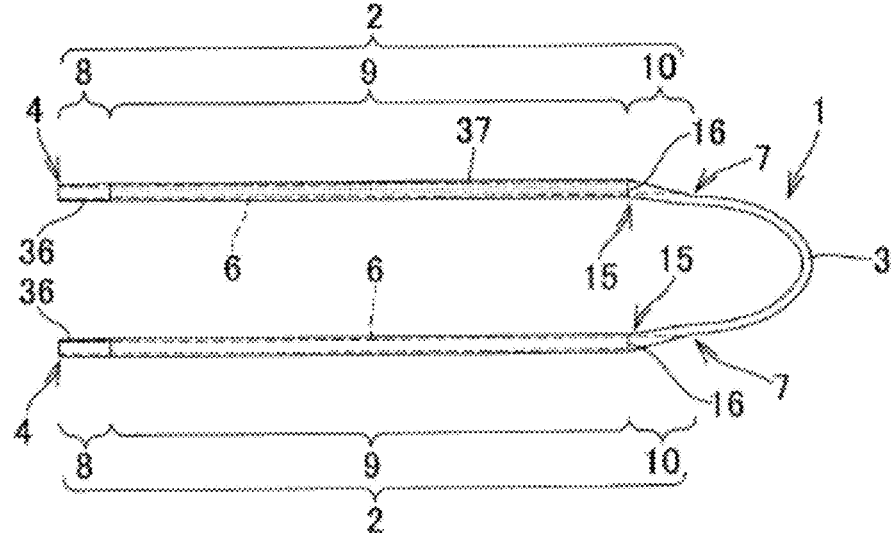

FIGS. 4(a), 4(b), and 4(c) illustrate an example of outer appearance of a lacrimal duct tube 1 of the present invention. FIG. 4(a) is a perspective view of the lacrimal duct tube 1, FIG. 4(b) is a side view of the lacrimal duct tube 1, and FIG. 4(c) is a top view of the lacrimal duct tube 1.

The lacrimal duct tube 1 is a lacrimal duct tube including a pair of tubular members 2 and a connection member 3 connecting ends of the tubular members 2.

Each of the tubular members 2 has an opening 5 at one end (leading end) 4, and the opening 5 communicates with a lumen 6. In addition, each of the paired tubular members 2 is connected to the connection member 3 at the other end side.

As illustrated in FIG. 4(c), each of the tubular members 2 is composed of a terminal end part 8, a main body 9, and a base end part 10 from the one end 4 to another end 7.

According to the present invention, in at least one of the tubular members 2, the base end part 10 including the other end 7 is tapered down toward the connection member 3.

Figure 5A:
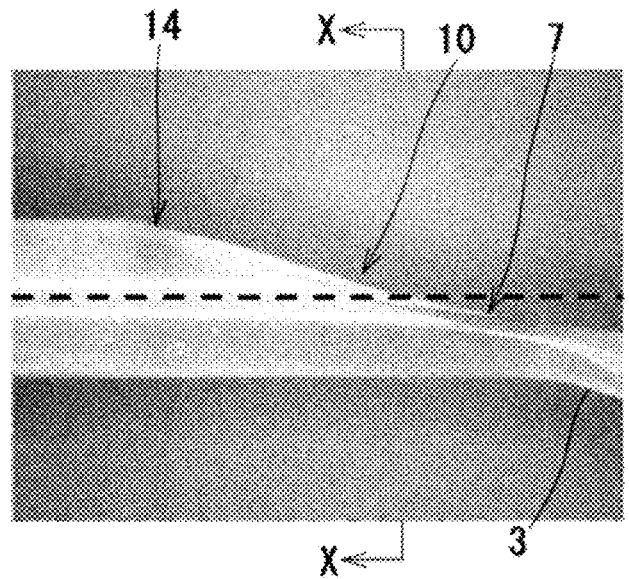
FIGS. 5(a) and 5(b) are schematic views of an example of a base end part of the lacrimal duct tube of the present invention.
Figure 5B:
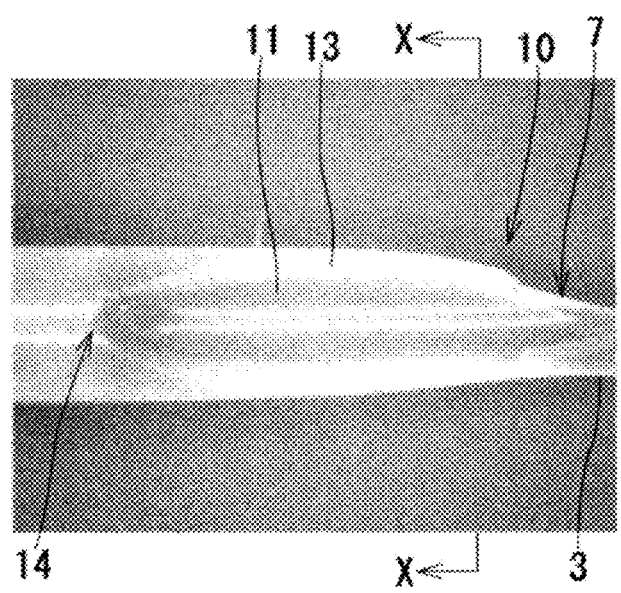
Figure 6:
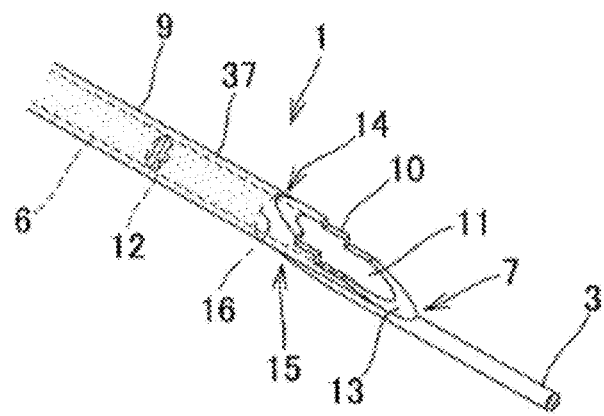
FIG. 6 is a schematic view of an example of the base end part of the lacrimal duct tube of the present invention.

The taper shape may be formed by cutting obliquely as illustrated in FIGS. 4(a), 5(a), 5(b), and 8(a) or may be provided with steps as illustrated in FIG. 6.

The base end part 10 has an inlet/outlet port 11 communicating with the lumen 6 of the tubular members 2.

The area of the inlet/outlet port 11 is adjusted to be larger than the area of an orthogonal cross section relative to the long-axis direction of the lumen 6 of the tubular member 2. For example, the area of the obliquely-cut step-less inlet/outlet port 11 as illustrated in FIGS. 4(a), 5(a), 5(b), and 8(a) and the area of inlet/outlet port 11 with steps as illustrated in FIG. 6 are larger than the area of an orthogonal cross section 12 relative to the long-axis direction of the lumen 6. The area of the inlet/outlet port 11 may be calculated from the video obtained by shooting the inlet/outlet port 11 and its surroundings with the use of a commercially available microscope at a plurality of angles or may be calculated using dedicated calculation software supporting three-dimensional shapes. In addition, the area of the cutting surface of the main body 9 of the tubular member 2 may be calculated as the area of the orthogonal cross section relative to the long-axis direction of the lumen 6 in the same manner as described above.

Figure 7:
FIG. 7 is a schematic view of an example of a cross section of the base end part of the lacrimal duct tube of the present invention.

The base end part 10 constituting a peripheral edge 13 of the inlet/outlet port 11 includes, on the other end side of the tubular member 2, a U-shaped portion in an orthogonal plane relative to the long-axis direction of the tubular member 2. For example, in the base end part 10 with the obliquely-cut step-less inlet/outlet port 11 as illustrated in FIGS. 5(a) and 5(b), the cross section at a position X on the other end side is U-shaped as illustrated in FIG. 7. Similarly, in the base end part 10 with the stepped inlet/outlet port 11 as illustrated in FIG. 6, the cross section at any position on the other end side is also U-shaped as illustrated in FIG. 7.

Figures 8A, 8B:
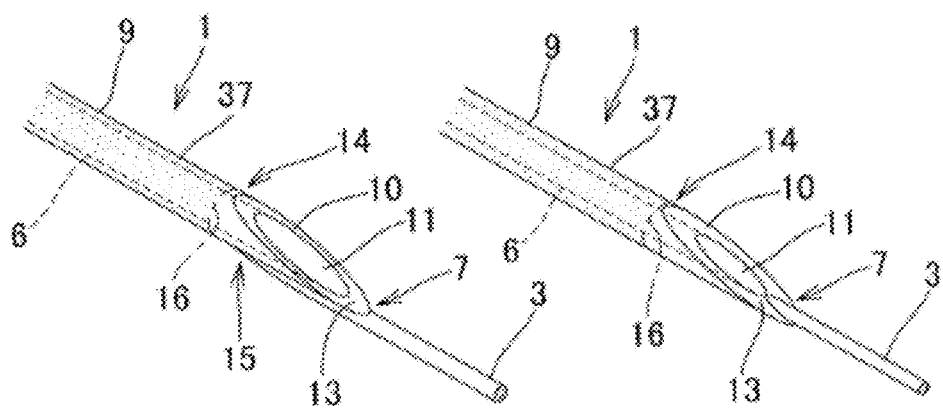
FIGS. 8(a) and 8(b) are schematic diagrams showing the state in which a tubular member and a connection member are connected at the base end part of the lacrimal duct tube of the present invention.

In the base end part 10 constituting the peripheral edge 13 of the inlet/outlet port 11, when a portion closest to the other end side (other end 7) and a portion closest to the one end side 14 in the peripheral edge 13 of the inlet/outlet port 11 are projected onto the orthogonal plane relative to the long-axis direction of the tubular member 2 as illustrated in FIGS. 4(b), 6, and 8(a), the distance between the portions on the orthogonal plane is preferably equal to or longer than the inner diameter of the tubular member 2 (diameter of the lumen 6).

In addition, a narrowest portion of the taper shape (the other end 7) of the base end part 10 projected onto the orthogonal plane relative to the long-axis direction of the tubular member 2 is preferably eccentric to the center of the orthogonal cross section of the base end part 10 relative to the long-axis direction.

In the lacrimal duct tube 1 of the present invention, a portion of the base end part 10 constituting the peripheral edge 13 of the inlet/outlet port 11 and the connection member 3 are connected together.

To connect the base end part 10 and the connection member 3, for example, the peripheral edge 13 of the base end part 10 and the end portion of the connection member 3 may be brought into abutment with each other as illustrated in FIG. 8(b). However, from the viewpoint of increasing the connection surface and the strength of the connection spot, the side surface of the base end part 10 constituting the peripheral edge 13 of the inlet/outlet port 11 and the side surface of the connection member 3 are preferably connected as illustrated in FIGS. 4(a), 6, and 8(a). The position of connection of the connection member 3 to the side surface of the base end part 10 and the main body 9 is preferably at the narrowest portion of the taper shape of the base end part 10 that is eccentric to the center of the orthogonal cross section of the base end part 10.

When the base end part 10 and the connection member 3 are connected by the side surfaces, the position of a leading end 15 of the connection member 3 may be near the other end 7 of the base end part 10. However, as illustrated in FIGS. 4(a), 4(c), 6, and 8(a), the position of a leading end 15 of the connection member 3 is preferably adjusted to be the position of the taper shape in the base end part 10 or be still closer to the one end side because the strength of the base end part 10 with the taper shape is reinforced and increased by the connection member 3.

In addition, although not illustrated, the position of the leading end 15 of the connection member 3 is more preferably adjusted to be still closer to the one end side than the connection portion 16 of the main body 9 and the base end part 10 of the tubular member 2 because the strength of the connection portion is also reinforced by the connection member 3.

The terminal end part 8, the main body 9, and the base end part 10 constituting the tubular member 2 may be provided as integral single-layer tubes or tubes with a layered structure in the thickness direction.

In particular, when the terminal end part 8 and the main body 9 of the tubular member 2 are formed from integral single-layer tubes and the base end part 10 is formed from a single material, the base end part 10 is preferably lower in hardness than the terminal end part 8 and the main body 9 as the remaining part of the tubular member 2.

As a tube with a layered structure, for example as illustrated in FIG. 9, a tubular member is configured such that the terminal end part 8 including the one end 4 has a single layer, and the main body 9 of the tubular member closer to the other end side than the terminal end part 8 has four layers. The tube constituting the terminal end part 8 forms an innermost layer 17 of the four-layer tube of the main body 9. In the main body 9, an inner intermediate layer 18, an outer intermediate layer 19, and an outermost layer 20 are stacked in this order on the innermost layer 17. FIG. 9(b) illustrates the cross section at the position X of the terminal end part 8 shown in FIG. 9(a), FIG. 9(c) illustrates the cross section at a position Y of the main body 9 shown in FIG. 9(a), and FIG. 9(d) illustrates the cross section at a position Z of the base end part 10. The number of the layers in the layered structure can be three or less or five or more. In the drawings, the terminal end part 8 and the base end part 10 are formed from single-layered tubes. Alternatively, they may be formed from tubes with a layered structure of two or more layers.

The outermost layer 20 in the multilayered structure is preferably formed from a material lower in hardness than the material for the innermost layer 17.

The outermost layer 20 in the multilayered structure is preferably formed from the same material as that for the base end part 10.

The lacrimal duct tube 1 configured as described above can be obtained by connecting the members such as the tubular member 2 and the connection member 3 and heating the connection portion to weld the resins of the members. There is no particular limitation on the procedure and method for thermally welding the members.

In the lacrimal duct tube 1 obtained as described above, the resins of the parts are thermally melted to form a smooth surface. For example, as illustrated in FIGS. 5(a) and 5(b), the members have a smooth surface including the connection portion between the connection member 3 and the base end part 10, and it is possible to significantly reduce the possibility that the lacrimal duct tube gets caught on the lacrimal duct wall when being inserted into the lacrimal duct.

Figure 10:
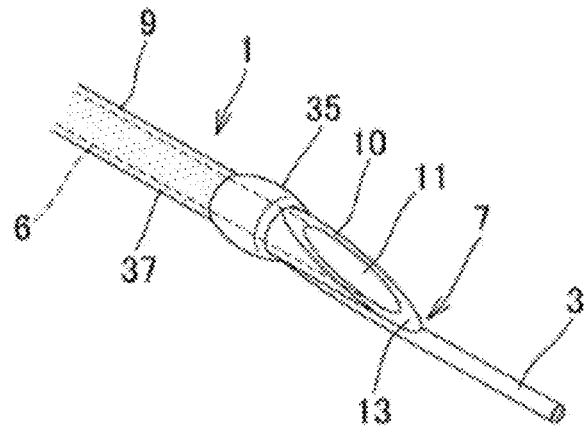
FIG. 10 is a schematic diagram showing an example of the lacrimal duct tube of the present invention.

In the lacrimal duct tube 1 of the present invention, as illustrated in FIG. 10, the circumference of the adjacent portions of the base end part 10 and the main body 9 as a portion of the remaining part of the tubular member 2 excluding the base end part 10 may be covered with a reinforcement member 35 across the base end part 10 and the main body 9 as a portion of the remaining part.

The reinforcement member 35 may be formed from the same material as that for the outermost layer 20 in the multilayered structure and the base end part 10. In addition, the reinforcement member 35 may be formed from the same material as that for the connection member 3.

The lacrimal duct tube 1 including the reinforcement member 35 can be fabricated according to the procedure illustrated in FIG. 11, for example.

Figure 11A:
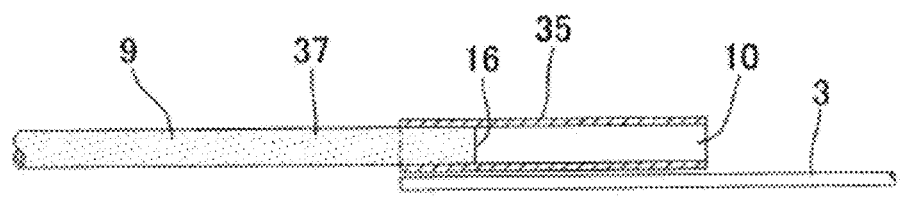
FIGS. 11(a) to 11(c) are schematic diagrams showing an example of a manufacturing process of the lacrimal duct tube of the present invention.

First, the other end surface of the tube for the main body 9 of the tubular member 2 and the end surface of the tube for the base end part 10 are brought into abutment with each other. Then, as illustrated in FIG. 11(a), the tube for the reinforcement member 35 is laid on the surfaces of the tube for the main body 9 and the tube for the base end part 10 including an abutment portion 16. The side surface of the connection member 3 is connected to the side surface of the tube for the reinforcement member 35. The outer peripheral parts of these tubes are heated with a tube for thermal welding to weld these members. The resins of the thermally welded portions are melted and integrated.

Figure 11B:
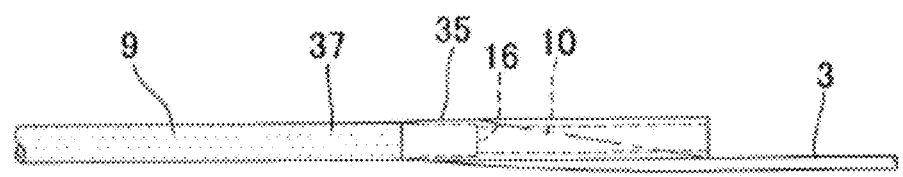
Figure 11C:
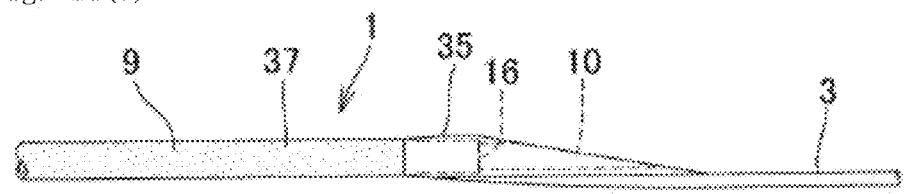

Then, as illustrated in FIG. 11(b), these members are cut by a cutting tool such as a cutter from an arbitrary position near the abutment portion 16 between the main body 9 and the base end part 10 to a position near the surface of adhesion to the connection member 3 at an arbitrary angle, thereby to obtain the lacrimal duct tube 1 with the reinforcement member 35 as illustrated in FIG. 11(c).

In the lacrimal duct tube 1 of the present invention, the terminal end part 8 including the one end 4 of at least one of the tubular members 2 may be formed from a colorless material.

A colored portion (line) 36 may be formed along the long-axis direction of the tubular member at a portion of the circumference of the terminal end part 8 formed from the colorless material as illustrated in FIGS. 4(a) and 4(c).

The colored portion 36 may be formed up to the one end 4 of the tubular member as illustrated in FIGS. 4(a) and 4(c), or may be shorter.

The shape of the colored portion 36 may be a line as illustrated in FIGS. 4(a) and 4(c), or may be a broken line as illustrated in FIGS. 12(a) and 12(b). FIG. 12(b) is an enlarged view of the terminal end part 8 and its surroundings of the tubular member 2 illustrated in FIG. 12(a).

The width of the colored portion 36 may be 1/50 to 1/3 of the entire circumferential length of the terminal end part 8. For example, as illustrated in FIGS. 13(a) and 13(b), even when the width of the colored portion 36 may be 1/3 of the entire circumferential length of the terminal end part 8, it is possible to check the inside of the lacrimal duct through the transparent wall portion other than the colored portion 36. FIG. 13(b) is an enlarged view of the terminal end part 8 and its surroundings of the tubular member 2 illustrated in FIG. 13(a).

The colored portion 36 may be formed on at least one of the same side as the inlet/outlet port 11 and the opposite side of the inlet/outlet port 11 in the circumferential direction of the tubular member 2. For example, the narrowest portion 7 of the taper shape in the base end part 10 eccentric to the center of the orthogonal cross section 12 of the base end part 10 and the main body 9 of the tubular member 2 may be positioned on the opposite side of the inlet/outlet port 11.

Specifically, in the lacrimal duct tube 1 illustrated in FIGS. 4(a) and 4(c), the colored portion 36 is formed on the opposite side of the inlet/outlet port 11 in the circumferential direction of the tubular member 2. When the position of the colored portion 36 illustrated in FIGS. 4(a) and 4(c) is shifted to the other side with the terminal end part 8 as a border in the direction of the orthogonal cross section relative to the long-axis direction, the colored portion 36 is formed on the same side as the inlet/outlet port 11 in the circumferential direction of the tubular member 2, although not illustrated in the drawings.

As illustrated in FIGS. 14(a) and 14(b), two colored portions 36a and 36b may be formed on the same side as the inlet/outlet port 11 and the opposite side of the inlet/outlet port 11 in the circumferential direction of the tubular member 2. In this case, as illustrated in FIG. 15, for example, the width of the colored portion 36a on the same side as the inlet/outlet port 11 is preferably different from the width of the colored portion 36b on the opposite side of the inlet/outlet port 11 (however, the widths of the colored portions 36 are not limited to them and the colored portions 36 with different widths may be positioned in reverse or the colored portions 36 with the same width may be formed). In this configuration, even when the terminal end part 8 is largely deformed during rupture into the obstructed site or the narrowed site in the lacrimal duct and becomes less recognizable by the lacrimal endoscope due to the transparency of the material, the two colored portions 36 make it possible to recognize the deformed state of the terminal end part 8 in a three-dimensional manner, recognize the position of the opening 5 by the lacrimal endoscope, and thus recognize the leading end position of the lacrimal endoscope. In addition, the orientation of the lacrimal duct tube can be recognized by the positional relationship between the colored portions 36a and 36b with different widths and the inlet/outlet ports 11. Accordingly, the lacrimal duct tube can be inserted in an accurate manner.

In addition, in one of the tubular members 2, another colored portion 37 may be provided on the entire circumference of the tubular member 2 closer to the other end side than the colored portion 36 (as a matter of course, the lacrimal duct tube may have the colorless portion 37 or the two tubular members may have the colored portions 37).

The colored portion 37 may be formed at least in the main body 9 of the tubular member 2 or may also be formed in the base end part 10 as well as illustrated in FIGS. 4(a) to 4(c). In addition, as in the lacrimal duct tube 1 illustrated in FIGS. 16(a) and 16(c), the both tubular members 2 may have the colored portions 37. The lacrimal duct tube 1 illustrated in FIGS. 16(a) to 16(c) is configured in the same manner as the lacrimal duct tube 1 illustrated in FIGS. 4(a) to 4(c) except that there are the two colored portions 37.

The hue of the colored portion 37 is preferably a complementary color hue or an adjacent complementary color hue relative to the hue of the colored portion 36 in the hue circle.

In particular, it is preferable that the color of the colored portion 37 of the tubular member 2 is yellow and the color of the colored portion 36 of the tubular member 2 is blue because the position of the tubular member 2 can be easily recognized in the dark lacrimal duct.

Figure 16A:
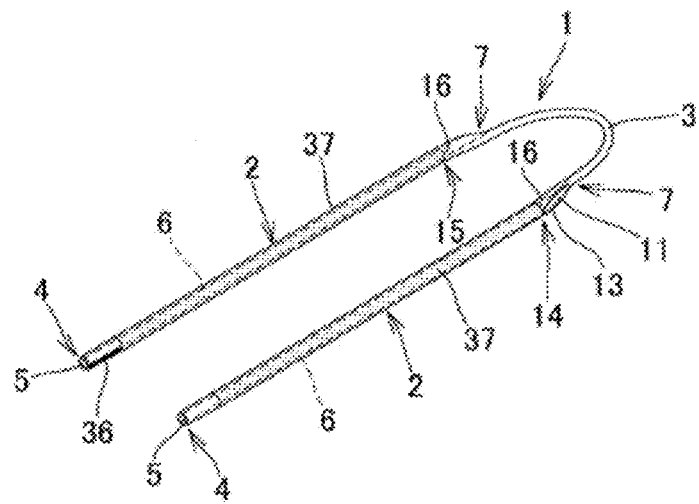
FIGS. 16(a) to 16(c) are schematic diagrams showing an example of the lacrimal duct tube of the present invention.
Figure 16B:
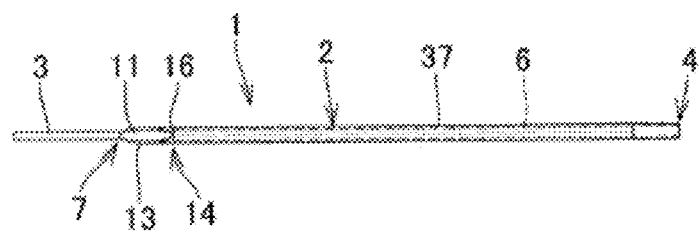
Figure 16C:
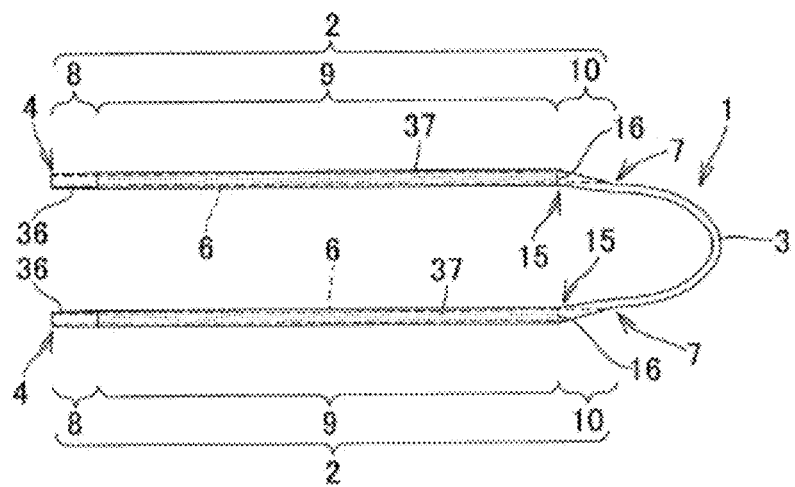

As in the lacrimal duct tube 1 illustrated in FIGS. 16(a) and 16(c), when the two tubular members 2 have the colored portions 37, the color of one colored portion 37 may be yellow, yellow green, or green, and the color of the other colored portion 37 may be identical to or different from the foregoing color.

In each of the lacrimal duct tubes 1 illustrated in FIGS. 12(a), 13(a), and 14(a), one of the tubular members 2 has the colored portion 37. Alternatively, the both tubular members 2 may have the colored portions 37 as illustrated in FIG. 16(a). In addition, when the two tubular members 2 have the colored portions 37, the color of one colored portion 37 may be yellow, yellow green, or green, and the color of the other colored portion 37 may be identical to or different from the foregoing color.

Figure 17A:
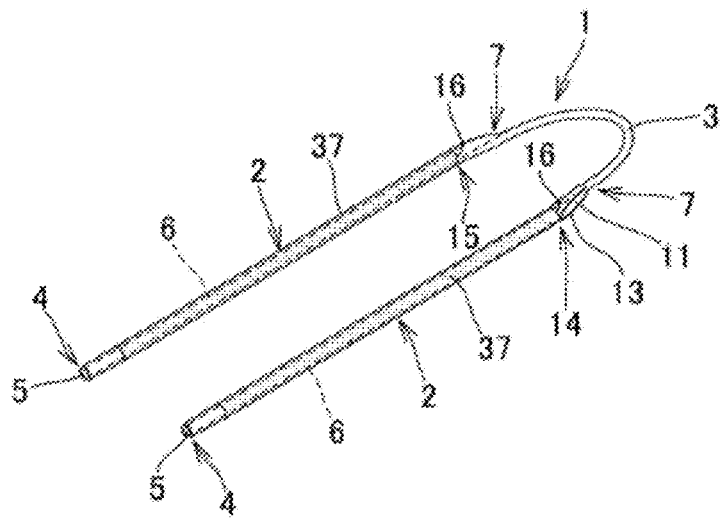
FIGS. 17(a) to 17(c) are schematic diagrams showing an example of the lacrimal duct tube of the present invention.
Figure 17B:
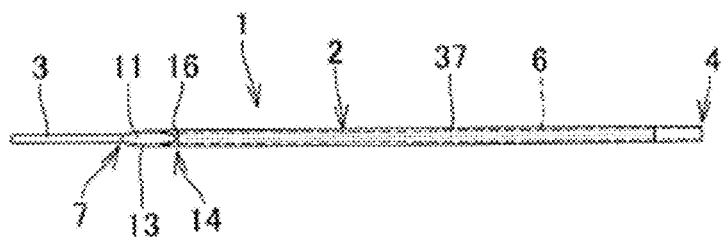
Figure 17C:
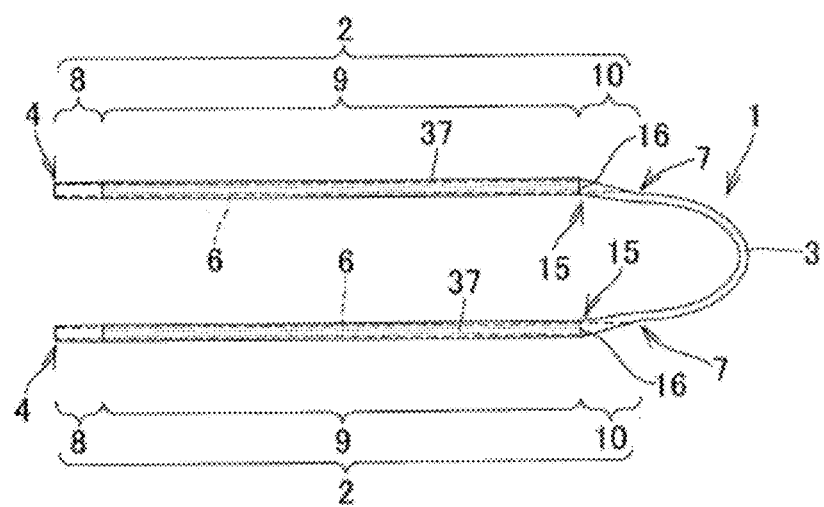

In addition, as illustrated in FIGS. 17(a) and 17(c), the lacrimal duct tube 1 may be configured such that the two tubular members 2 have the colored portions 37 and do not have the colored portion 36 at the terminal end parts. The lacrimal duct tube 1 illustrated in FIGS. 17(a) to 17(c) is configured in the same manner as the lacrimal duct tube 1 illustrated in FIGS. 16(a) to 16(c) except that the colored portions 36 are not provided.

In the lacrimal duct tube 1 illustrated in FIGS. 17(a) and 17(c), the color of one colored portion 37 may be yellow, yellow green, or green, and the color of the other colored portion 37 may be identical to or different from the foregoing color.

The colored portion 36 may not be provided as described above, and the terminal end part may be formed from not a transparent or colorless material but from a see-through material (for example, a translucent blue material) to a degree that the state of the outside of the tube can be observed by the lacrimal endoscope through the wall portion of the terminal end part. This is because, when the two tubular members have the colored portions, the position of the tubular member first inserted into the lacrimal duct can be checked by the lacrimal endoscope in the tubular member inserted later (for example, from the terminal end part), thereby making it possible to check the tubular member in a more accurate manner even in the dark lacrimal duct and enhance the position accuracy of the tubular member to be placed later in the lacrimal duct.

In another mode of lacrimal duct tube, one end of the tubular member may be a blind end.

Specifically, the lacrimal duct tube includes: a pair of tubular members that is each closed at one end and has an opening at the other end; and a connection member connecting the other ends of the tubular members, wherein a base end part including the other end of at least one of the tubular members is tapered down toward the connection member and the base end part has an inlet/outlet port communicating with the lumen of the tubular member, and a portion of the base end part constituting peripheral edge of the inlet/outlet port and the connection member are connected together.

The configurations of the components of the lacrimal duct tube of the present embodiment, for example, the configuration of the tubular members, the configuration of the terminal end part at the one end of the tubular member, the configuration of the opening formed at the other end, and the configuration of the connection member connecting the other ends of the tubular members may be the same as those of the foregoing components of the lacrimal duct tube having an opening at the one end side.

As the lacrimal duct tube having the opening at the one end side described above, the lacrimal duct tube of the embodiment can receive a bougie or a lacrimal endoscope inserted into the tubular member from the inlet/outlet port of the base end part as the other end, thereby allowing the operator to operate the bougie to guide the lacrimal duct tube into the lacrimal duct and place the lacrimal duct tube in the lacrimal duct. In addition, by shaping the tubular member in such a manner that the base end part is easy to grasp by forceps and is hard to damage the lacrimal duct even in contact with the lacrimal duct, the lacrimal duct tube is unlikely to get tucked or damaged during operation in the lacrimal duct, and is excellent in procedure in the lacrimal duct and operability of the attached bougie.

In addition, the leading end of the connection member is closer to the one end side than the position of the taper shape formed at the other end side as the base end part. Accordingly, the strength of the connection portion between the end of the tube and the opening and its surroundings at the other end can be reinforced by the connection member.

In particular, in the lacrimal duct tube of the embodiment, the one end of the tubular member is a closed blind end. Accordingly, when a bougie or a lacrimal endoscope is inserted into the tubular member from the inlet/outlet port of the base end part to a portion near the one end, and is inserted into the lacrimal duct, it is possible to improve the bougie and the lacrimal duct tube in pushability, and advantageously easily obtain the pushability for rupture into the obstructed site.

In the lacrimal duct tube of the embodiment, the terminal end part including the one end of at least one of the tubular members is formed from a colorless material. Accordingly, when the leading end of the lacrimal endoscope is inserted into a portion near the terminal end part, it is possible to secure the viewing field of the lacrimal endoscope from the terminal end part of the tubular member via the tubular member. For example, when the probe of the lacrimal endoscope is inserted into and attached to the transparent tubular member from the inlet/outlet port of the base end part to a portion near the opening, and then is inserted into the lacrimal duct from the lower punctum through the lower canaliculus, the position of the tubular member first inserted can be easily recognized by finding the yellow-colored portion even in the dark lacrimal sac and nasolacrimal duct. In addition, the position of the inferior nasal meatus into which the tube is to be inserted can also be easily recognized by checking the orientation of the yellow-colored portion.

Figure 18A:
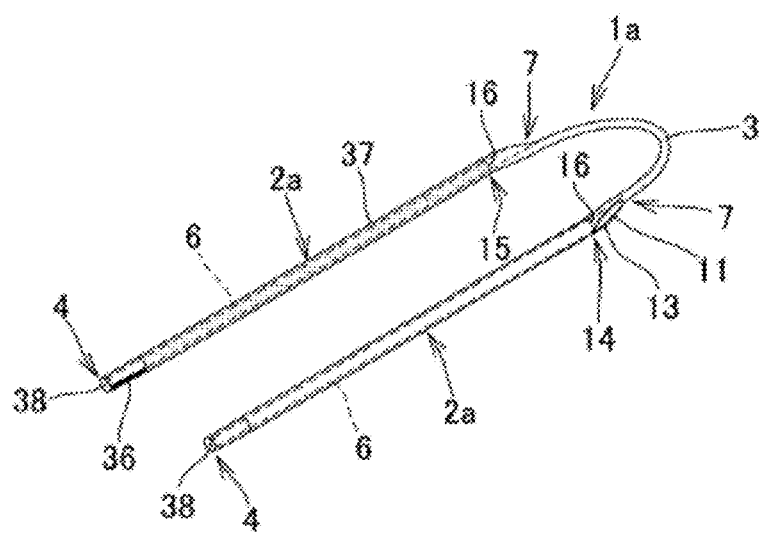
FIGS. 18(a) to 18(c) are schematic diagrams showing an example of the lacrimal duct tube of the present invention.
Figure 18B:
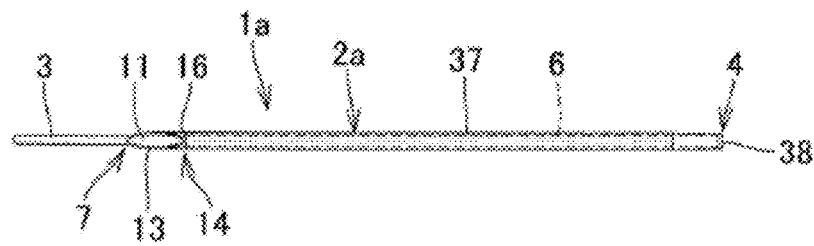
Figure 18C:
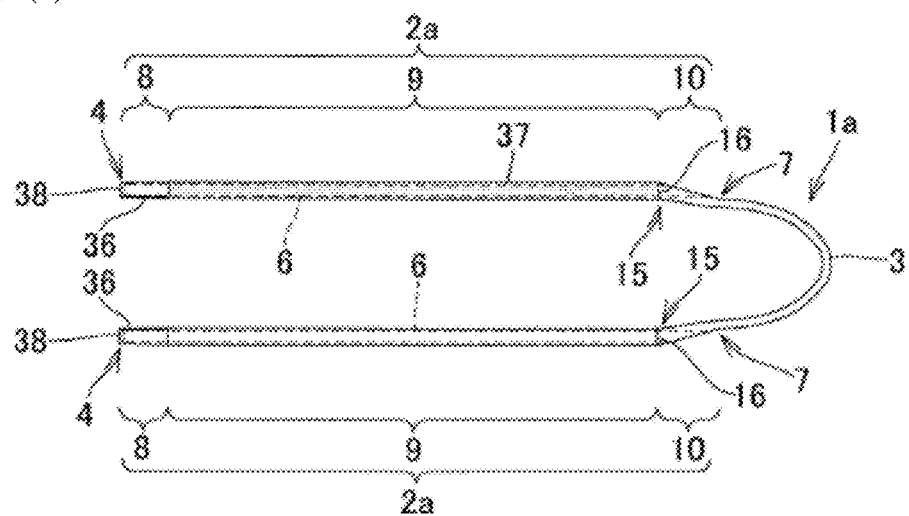

The embodiment is the same as the example illustrated in FIG. 4 except that the one end (leading end) 4 of each tubular member 2a constituting a lacrimal duct tube 1a has no opening but is closed to form a blind end 38 as illustrated in FIGS. 18(a), 18(b), and 18(c). The configurations of the base end part 10 and the inlet/outlet port 11 not illustrated are the same as those of the examples illustrated in FIGS. 6, 7, 8, 10, and 11. The configurations of the terminal end part 8 and the main body 9 are the same as those of the example illustrated in FIG. 9. The configuration of the colored portion 36 at the terminal end part 8 is the same as those of the examples illustrated in FIGS. 12, 13, 14, and 15. Therefore, the differences between the embodiments and particularly preferable examples will be described below, and the same members are given the same reference signs and descriptions thereof will be omitted.

FIGS. 18(a), 18(b), and 18(c) illustrate an example of outer appearance of the lacrimal duct tube 1a of the embodiment. FIG. 18(a) is a perspective view of the lacrimal duct tube 1a, FIG. 18(b) is a side view of the lacrimal duct tube 1a, and FIG. 18(c) is a top view of the lacrimal duct tube 1a.

The lacrimal duct tube 1a includes a pair of tubular members 2a that each has the closed blind end 38 at one end and the connection member 3 connecting ends of the tubular members 2a.

Figure 19:
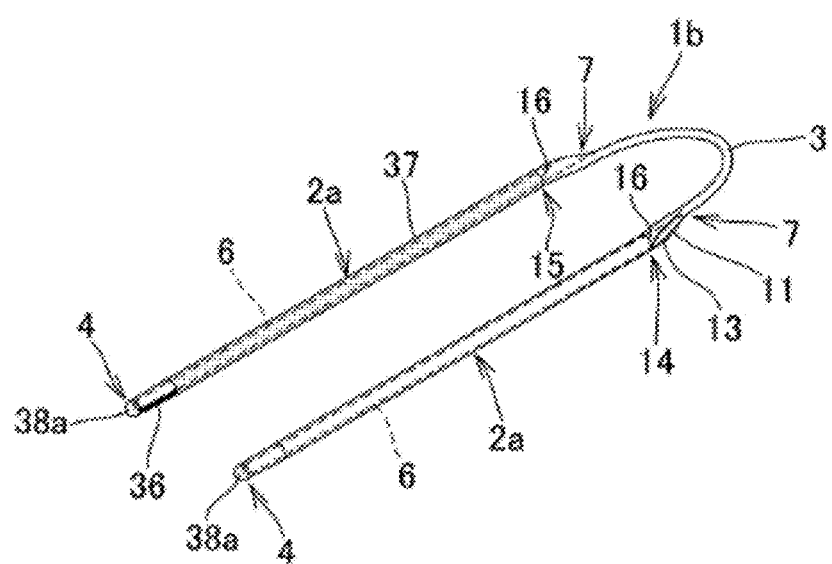
FIG. 19 is a schematic diagram showing an example of the lacrimal duct tube of the present invention.

The terminal end part 8 constituting the one end of the tubular member 2a has a lumen and the closed blind end 38 at the one end side. The terminal end part 8 may be a tube that has a lumen and is closed in advance at an end portion, for example. Alternatively, the one end of the tubular member 2a may be closed in such a manner that a resin rod for leading end is abutted and thermally welded with the leading end of the tubular terminal end part 8, and then the one end of the rod for leading end is cut and the lumen of the tubular terminal end part 8 is closed at the leading end portion. Otherwise, the cut rod for leading end may be further rounded to form a round blind end portion 38a as in the lacrimal duct tube 1b illustrated in FIG. 19. The lacrimal duct tube 1b illustrated in FIG. 19 is the same as the example illustrated in FIG. 18(a) except that the round blind end portion 38a is formed at the one end (leading end) 4 of the tubular member 2a.

The terminal end part 8 including the one end of the tubular member 2a is preferably formed from a colorless material because, when the leading end of the lacrimal endoscope is inserted into a portion near the terminal end part 8, it is possible to secure the viewing field of the lacrimal endoscope from the lumen of the terminal end part 8.

Further, when the probe of the lacrimal endoscope is inserted into and attached to the tubular member 2a with the transparent main body 9 from the inlet/outlet port 11 of the base end part 10 to a portion near the terminal end part 8, and then is inserted into the lacrimal duct from the lower punctum through the lower canaliculus, the position of the tubular member 2a first inserted can be easily recognized by finding the yellow-colored portion even in the dark lacrimal sac and nasolacrimal duct. In addition, the position of the inferior nasal meatus into which the tube is to be inserted can also be easily recognized by checking the orientation of the yellow-colored portion 36.

EXAMPLES

Example 1

A lacrimal duct tube having the tubular members 2 of the structure illustrated in FIG. 11 was fabricated in such a manner as described below.

First, a polyurethane tube for base end part of the same diameter was abutted with the other end of a tube in which the terminal end part had a single layer and the main body had a four-layer structure, and a tube for reinforcement member was laid on the surfaces of the tube for main body of the four-layer structure and the tube for base end part including the abutted portions. The side surface of a rod for connection member was connected to the side surface of the tube for reinforcement member, the position of the leading end of the rod was adjusted to come closer to the one end side than the abutted surfaces, and then the connection portions of the tubes were thermally welded.

Then, the base end part was obliquely cut from a portion near the one end to a portion near the other end to form the inlet/outlet port, thereby fabricating the lacrimal duct tube having the pair of tubular members and the connection member.

The components of the used members are as follows:
(Tubular Members)
(1) Terminal End Part
  Low-Density Polyethylene
  Length of the terminal end part: about 4 mm, tapered down with a diameter of 0.9 to 1.3 mm
(2) Main Body
  Innermost layer: low-density polyethylene, inner intermediate layer: high-density polyethylene, outer intermediate layer: adhesive low-density polyethylene, and outermost layer: polyurethane
  Diameter of lumen: 0.96 mm
  The terminal end parts and the main bodies of the tubular members were in a see-through state to a degree that they could be observed by the lacrimal endoscope even from the lumen.
(3) Base End Part
  Polyurethane
  Inner diameter: 0.96 mm, length: 5 mm (Connection Member)
Polyurethane
Diameter: 0.7 mm
Entire length: 23 mm Comparative Example 1

Without using a tube for base end part, the side surface of the connection member was connected and thermally welded to the side surface of the other end of a tube in which the terminal end part had a single layer and the main body had a four-layered structure, and the other end of the tubular member was obliquely cut, thereby fabricating the lacrimal duct tube without the base end part unlike the lacrimal duct tube of the example 1.

The materials for the parts were the same as those for the parts in the example 1.

Comparative Example 2

In the lacrimal duct tube of the example 1, the connection position of a solid rod to be the connection member was adjusted and positioned on the central axis of an orthogonal cross section of a tube for main body of a four-layer structure, and then these members were thermally welded. Then, the side surface of the base end part was perforated by a punch to form a hole as an inlet/outlet port, thereby fabricating the lacrimal duct tube in which the base end part was not tapered.

Test Example 1

A lacrimal endoscope was inserted into the lacrimal duct tubes of the example 1 and the comparative examples 1 and 2 from the inlet/outlet port up to a portion near the opening of the tubular member. Then, these members were inserted into an artificial lacrimal duct model to perform a procedure using forceps in the same manner as actual SEP. The forceps were used to grasp the base end parts of the lacrimal duct tubes of the example 1 and the comparative example 2, and grasp the cut portion of the tubular member of the lacrimal duct tube of the comparative example 1.

As the result, the lacrimal duct tube of the example 1 could be favorably placed in the artificial model.

Meanwhile, the lacrimal duct tube of the comparative example 1 was broken at the cut tube portion in the middle of the course, and the adhesion surfaces of the outer intermediate layer and the outermost layer separated from each other to expose all the cross sections of the polyethylene layers to the outside.

In addition, the lacrimal duct tube of the comparative example 2 was not broken at the base end part as in the comparative example 1, but the lacrimal endoscope and the polyurethane surface got tucked during the procedure, and it took a long time to complete the placement.

Test Example 2

The two tubular members 2 in the lacrimal duct tube of the example 1 were provided with blue-colored portion 36 formed at the terminal end part 8 up to the one end on the same side as the connection surface of the rod of the connection member 3 (opposite side of the inlet/outlet port 11 of the base end part 10). The colored portions 36 were lines that were adjusted to have a width of ⅒ of the entire circumferential length of the terminal end part.

In one of the tubular members, the entire circumference of the main body 9 from the colored portion 36 to the other end side was colored yellow.

The colored lacrimal duct tube was placed in a real lacrimal duct by the same insertion surgery as SEP.

First, the probe of the lacrimal endoscope was inserted into and attached to the yellow-colored tubular member from the inlet/outlet port of the base end part to a portion near the opening, and then the lacrimal duct tube was inserted into the real lacrimal duct from the upper lacrimal punctum through the upper lacrimal canaliculus to the inferior nasal meatus. The state of the lacrimal duct could be observed and recognized from the opening of the tubular member in the lacrimal duct tube. In addition, the lacrimal duct tube could be reliably inserted into the desired place such as the obstructed site without going in the wrong direction by checking the orientation of the colored portion of the tubular member. After checking that the tip of the lacrimal duct tube came out of the inferior nasal meatus, the lacrimal endoscope was removed to place the lacrimal duct tube in the lacrimal duct.

Subsequently, the probe of the lacrimal endoscope was inserted into and attached to the transparent tubular member from the inlet/outlet port of the base end part to a portion near the opening, and then is inserted into the lacrimal duct from the lower punctum through the lower canaliculus. The position of the tubular member first inserted could be easily recognized by finding the yellow-colored portion even in the dark lacrimal sac and nasolacrimal duct. In addition, the position of the inferior nasal meatus into which the tube was to be inserted could also be easily recognized by checking the orientation of the yellow-colored portion.

Test Example 3

The two tubular members 2 in the lacrimal duct tube of the example 1 were provided with linear blue colored portions 36*a* and 36*b* on the surface of the terminal end part 8 on the same side as the inlet/outlet port 11 of the base end part 10 and the opposite side of the inlet/outlet port 11 of the base end part 10 up to the one end 4 as illustrated in FIGS. 14(*a*) and 14(*b*). As illustrated in FIG. 15, the width of the colored portion 36*a* on the same side as the inlet/outlet port 11 was adjusted to be smaller than the width of the colored portion 36*b* on the opposite side of the inlet/outlet port 11. The other configurations were the same as those of the test example 2.

As with the test example 2, the colored lacrimal duct tube was placed in a real lacrimal duct by the same insertion surgery as SEP. During rupture into the obstructed site in the lacrimal duct, the terminal end part largely deformed but the presence of the two colored portions in a diagonal relationship in a circumferential direction at the terminal end made it possible to perform the insertion surgery while recognizing accurately the state of deformation of the terminal end part and the positional relationship between the opening and the lacrimal endoscope. Of the two colored portions, the colored portion on the same side as the inlet/outlet port 11 was decreased in width, and therefore the lacrimal duct tube could be reliably inserted into the desired place without going in the wrong direction while checking the orientation of the lacrimal duct tube.

Example 2

The lacrimal duct tube having a narrow terminal end part was fabricated in such a manner like the example 1 as described above. The narrow terminal end was positioned at the opening side. After the lacrimal duct tube of the example 1 is fabricated, a mandrel in the shape of a rod having a 0.7 mm outer diameter was pushed into the terminal end part of the tubular member from the opening. After that, the tip of the tubular members were thermally compressed using a shrink tube to form a narrow terminal end part (0.5 mm long) with a 0.7 mm inner diameter.

The components of the used members are as follows:
(Tubular Members)
(1) Terminal End Part
   Low-density polyethylene
   Length of the terminal end part: about 4 mm, tapered down with a diameter of 0.9 to 1.3 mm.
   In the terminal end part, a lumen has the inside diameter part that got narrow to 0.7 mm in diameter in the section of 0.5 mm in length from the opening at extreme tip end.
(2) Main Body
   Innermost layer: low-density polyethylene, inner intermediate layer: low-density polyethylene, outer intermediate layer: adhesive low-density polyethylene, and outermost layer: polyurethane
   Diameter of lumen: 0.96 mm
   The terminal end parts and the main bodies of the tubular members were in a see-through state to a degree that they could be observed by the lacrimal endoscope even from the lumen.
(3) Base End Part
   Polyurethane
   Inner diameter: 0.96 mm, length: 5 mm
(Connection Member)
   Polyurethane
   Diameter: 0.7 mm
   Entire length: 23 mm Example 3

The lacrimal duct tube 1*b* having the tubular members 2*a* of the structure illustrated in FIG. 19 was fabricated in such a manner as described below.

First, a polyurethane tube for base end part of the same diameter was abutted with the other end of a tube in which the terminal end part 8 had a single layer and the main body 9 had a four-layer structure, and a tube for reinforcement member was laid on the surfaces of the tube for main body of the four-layer structure and the tube for base end part including the abutted portions. The side surface of a rod for connection member was connected to the side surface of the tube for reinforcement member, and the position of the leading end of the rod was adjusted to come closer to the one end side than the abutted surfaces, and then the connection portions of the tubes were thermally welded. Accordingly, the leading end of the connection member 3 was arranged at the same position as the one end side of the tube for reinforcement member.

Then, the base end part 10 was obliquely cut by scissors from a portion near the one end side to a portion near the other end side to form the inlet/outlet port 11, thereby fabricating the lacrimal duct tube 1*b* with a pair of tubular members 2*a* and the connection member 3. The scissors were first put into a portion closer to the other end side than the leading end part of the rod for connection member. The scissors were lastly applied to a portion closer to the connection member than the one end of the tube for reinforcement member.

Further, a polyethylene rod for leading end part with inner and outer diameters equal to or smaller than those of the tube was abutted with and thermally welded to the one end of the tubular member 2*a*. The one end of the rod for leading end part was cut and rounded, thereby fabricating the lacrimal duct tube 1*b* with the blind end portion 38*a*.

The components of the used members are as follows:
(Tubular Members)
(1) Terminal End Part
   Low-density polyethylene
   Length of the terminal end part: about 4 mm, tapered down with a diameter of 0.9 to 1.3 mm
(2) Main Body
   Innermost layer: low-density polyethylene, inner intermediate layer: low-density polyethylene, outer intermediate layer: adhesive low-density polyethylene, and outermost layer: polyurethane
   Diameter of lumen: 0.96 mm
   The terminal end parts of the tubular members were in a see-through state to a degree that they could be observed by the lacrimal endoscope even from the lumen.
(3) Base End Part
   Polyurethane
   Inner diameter: 0.96 mm, length: 5 mm
(4) Rod for Leading End Part
   Polyethylene
   Outer diameter: 0.86 mm, length: 1 mm
(Connection Member)
   Polyurethane
   Diameter: 0.7 mm
   Entire length: 23 mm A bougie and a lacrimal endoscope could be inserted into the obtained lacrimal duct tube 1*b* from the inlet/outlet port 11 of the base end part 10 as the other end of the tubular member 2*a*. The operator could operate the bougie to guide the lacrimal duct tube 1*b* into the lacrimal duct and place the lacrimal duct tube 1*b* in the lacrimal duct. In addition, the base end part 10 was easy to grasp by forceps and was hard to damage even in contact with the lacrimal duct. Accordingly, the lacrimal duct tube 1*b* was unlikely to tuck or break even during operation in the lacrimal duct, and was excellent in procedure in the lacrimal duct and operability of the attached bougie.

In addition, the leading end of the connection member 3 was positioned closer to the one end 4 side than the taper shape formed on the other end 7 side of the base end part 10, and the strength of the connection portion between the main body 9 of the lacrimal duct tube 1*b* and a portion near the opening 5 in the other end 7 were reinforced by the connection member 3.

REFERENCE SIGNS LIST 1, 1*a*, and 1*b* Lacrimal duct tube
2 and 2*a* Tubular member
3 Connection member
4 One end
5 Opening
6 Lumen
7 Other end
8 Terminal end part
9 Main body
10 Base end part
11 Inlet/outlet port
12 Orthogonal cross section
13 Peripheral edge of inlet/outlet port 11
14 Portion closest to one end side of peripheral edge 13 of inlet/outlet port 11
15 Leading end of connection member 3

16 Connection portion
17 Innermost layer
18 Inner intermediate layer
19 Outer intermediate layer
20 Outermost layer
21 Upper lacrimal punctum
22 Lower lacrimal punctum
23 Upper lacrimal canaliculus
24 Lower lacrimal canaliculus
25 Common canaliculus
26 Lacrimal sac
27 Nasolacrimal duct
28 Inferior nasal meatus
29 Lacrimal endoscope
30 Sheath
31 Lacrimal duct
32 Obstructed site
33 Lacrimal duct tube
35 Reinforcement member
36 Colored portion
37 Colored portion closer to other end side than colored portion 36
38 Blind end
38a Blind end part
X, Y, and Z Direction orthogonal to long-axis direction of tubular member

The invention claimed is:

1. A lacrimal duct tube comprising:
a pair of first and second tubular members that each have a lumen, at a first end an opening, and a port at a second end, the opening and the port communicating with each other through the lumen; and
a connection member that connects the second end of each of the first and second tubular members, wherein
a side surface of the connection member contacts with a side surface of each second end portion of the first and second tubular members such that the connection member connects the first and second tubular members,
a base end part including the second end of at least one of the first and second tubular members is cut to have a taper shape down toward the connection member so that the base end part has the port which communicates with the opening through the lumen and the port is defined by a peripheral edge of a cross section formed by cutting the base end part,
a portion of the base end part constituting peripheral edge of the port and the connection member are connected together,
a side surface of the base end part constituting the peripheral edge of the port and a side surface of the connection member are connected together, and
a position of a leading end of the connection member is adjusted to be a position, from which the taper shape tapers downward to the connection member and which is formed in the base end part in an axial direction.

2. The lacrimal duct tube according to claim 1, wherein the base end part is formed of material different from material of a remaining portion of the first and the second tubular members except the base end part.

3. The lacrimal duct tube according to claim 2, wherein the base end part and the remaining portion are welded.

4. The lacrimal duct tube according to claim 2, wherein at least a part of the remaining portion has a multilayered structure.

5. The lacrimal duct tube according to claim 4, wherein an outermost layer in the multilayered structure and the base end part are formed from the same material.

6. The lacrimal duct tube according to claim 4, wherein an outermost layer in the multilayered structure is formed from a material lower in hardness than an innermost layer.

7. The lacrimal duct tube according to claim 2, wherein the base end part is formed from a single material and is lower in hardness than the remaining portion.

8. The lacrimal duct tube according to claim 2, wherein the base end part and the remaining portion are covered by a reinforcement member.

9. The lacrimal duct tube according to claim 8, wherein
at least a part of the remaining portion has a multilayered structure, and
the reinforcement member, an outermost layer in the multilayered structure, and the base end part are formed from the same material.

10. The lacrimal duct tube according to claim 8, wherein
at least a part of the remaining portion has a multilayered structure, and
the connection member, the reinforcement member, an outermost layer in the multilayered structure, and the base end part are formed from the same material.

11. The lacrimal duct tube according to claim 2, wherein an area of the port is larger than an area of an orthogonal cross section of the lumen of the first or second tubular member with respect to a longitudinal axis direction.

12. The lacrimal duct tube according to claim 2, wherein, when a portion of the peripheral edge of the port closest to a second end side and a portion of the peripheral edge of the port closest to a first end side are projected onto an orthogonal plane with respect to the longitudinal axis direction of the first or second tubular member,
the distance between the portions on the orthogonal plane is larger than the length of inner diameter of the first or second tubular member.

13. The lacrimal duct tube according to claim 2, wherein the base end part constituting the peripheral edge of the port includes a U-shaped portion in the orthogonal plane with respect to the longitudinal axis direction of the first or second tubular member on the second end side of the first or second tubular member.

14. The lacrimal duct tube according to claim 2, wherein the peripheral edge of the port has a step-less surface.

15. The lacrimal duct tube according to claim 2, wherein, when being projected onto the orthogonal plane with respect to the longitudinal axis direction of the first or second tubular member, the narrowest portion of the taper shape in the base end part is located apart from a center of an orthogonal cross section of the base end part with respect to the longitudinal axis direction.

16. The lacrimal duct tube according to claim 2, wherein a circumference of adjacent portions of the base end part and the remaining portion of the first or second tubular member excluding the base end part is covered with a reinforcement member across the base end part and the remaining portion.

17. The lacrimal duct tube according to claim 2, wherein a terminal end part including a first end of at least one of the first or second tubular members is formed from a colorless material.

18. The lacrimal duct tube according to claim 17, wherein a colored portion is formed at a portion of the circumference of the terminal end part formed from the colorless material along a longitudinal axis direction of the first or second tubular member.

19. The lacrimal duct tube according to claim 18, wherein the colored portion is formed up to the first end.

20. The lacrimal duct tube according to claim 18, wherein the colored portion is in a shape of a line or broken line.

21. The lacrimal duct tube according to claim 18, wherein the colored portion has a width of ⅟₅₀ to ⅓ of an entire circumferential length of the terminal end part.

22. The lacrimal duct tube according to claim 18, wherein the colored portion in the first or second tubular member is formed on at least one of the same side as the port and the opposite side of the port in a circumferential direction of the first or second tubular member.

23. The lacrimal duct tube according to claim 18, wherein the colored portion with a smaller width is formed on the same side as the port in the circumferential direction of the first or second tubular member, and the colored portion with a larger width is formed on the opposite side of the port in the circumferential direction of the first or second tubular member.

24. The lacrimal duct tube according to claim 18, wherein a hue of one of the pair of the first and second tubular members has a hue having a complementary color or an adjacent complementary color relative to a hue of the colored portion in a color circle.

25. The lacrimal duct tube according to claim 18, wherein a color of a colored first or second tubular member is yellow, and the color of the colored portion is blue.

26. The lacrimal duct tube according to claim 17, wherein
at least two colored portions are formed at a portion of the circumference of the terminal end part formed from the colorless material along a longitudinal axis direction of the first or second tubular member, and
one of the at least two colored portions is formed on the same side as the port and the other of the at least two colored portions is formed on the opposite side of the port in a circumferential direction of the first or second tubular member, and a width of said one of the at least two colored portions is different from a width of the other of the at least two colored portions.

* * * * *